(12) United States Patent
Meshulam et al.

(10) Patent No.: US 11,780,237 B2
(45) Date of Patent: Oct. 10, 2023

(54) METHOD AND APPARATUS FOR PRINTING ON A DRINK

(71) Applicant: Ripples LTD., Petah Tikva (IL)

(72) Inventors: Yosef Meshulam, Kochav Yair (IL); Marc Van Dyke, Bet Shemesh (IL); Eyal Eliav, Tel Aviv (IL)

(73) Assignee: RIPPLES LTD, Petah Tikva (IL)

( * ) Notice: Subject to any disclaimer, the term of this patent is extended or adjusted under 35 U.S.C. 154(b) by 740 days.

(21) Appl. No.: 16/311,881

(22) PCT Filed: Jun. 23, 2017

(86) PCT No.: PCT/IB2017/000991
§ 371 (c)(1),
(2) Date: Dec. 20, 2018

(87) PCT Pub. No.: WO2017/221077
PCT Pub. Date: Dec. 28, 2017

(65) Prior Publication Data
US 2019/0200799 A1 Jul. 4, 2019

Related U.S. Application Data

(60) Provisional application No. 62/183,695, filed on Jun. 23, 2015, provisional application No. 62/354,093, filed on Jun. 23, 2016.

(51) Int. Cl.
*B41J 3/407* (2006.01)
*B41M 5/00* (2006.01)
*G01N 33/14* (2006.01)
*A47J 31/44* (2006.01)
*G06Q 30/0601* (2023.01)
*B41J 2/01* (2006.01)
*A47J 31/00* (2006.01)

(52) U.S. Cl.
CPC .......... *B41J 3/407* (2013.01); *A47J 31/4496* (2013.01); *B41M 5/0047* (2013.01); *G01N 33/14* (2013.01); *G06Q 30/0601* (2013.01); *A47J 31/002* (2013.01); *B41J 2/01* (2013.01); *B41J 3/4073* (2013.01); *B41J 2203/01* (2020.08)

(58) Field of Classification Search
CPC ...... B41J 3/407; B41J 3/4073; B41J 2203/01; B41M 5/0047; G01N 33/14; A47J 31/002
See application file for complete search history.

(56) References Cited

U.S. PATENT DOCUMENTS

| | | | | |
|---|---|---|---|---|
| 8,753,702 B2 * | 6/2014 | Baker | ................. | A23G 3/0097 426/383 |
| 8,763,918 B2 * | 7/2014 | Lillard, Jr. | ............ | G06F 16/284 235/494 |
| 9,483,957 B1 * | 11/2016 | Fuemmeler | ............ | G09B 5/125 |
| 10,813,488 B2 * | 10/2020 | Lavie | ....................... | A23F 5/465 |
| 2005/0029287 A1 * | 2/2005 | Mobbs | ................. | B67D 1/0024 222/1 |

(Continued)

FOREIGN PATENT DOCUMENTS

| | | | | | |
|---|---|---|---|---|---|
| JP | 2014167716 A | * | 9/2014 | .............. | G09B 5/02 |
| WO | WO-2016021906 A1 | * | 2/2016 | .............. | B65D 25/00 |

*Primary Examiner* — Jill E Culler
(74) *Attorney, Agent, or Firm* — Marc Van Dyke; Momentum IP

(57) ABSTRACT

A method and device of providing a customized drink and/or printing on a drink.

20 Claims, 39 Drawing Sheets

(56) References Cited

U.S. PATENT DOCUMENTS

| | | | |
|---|---|---|---|
| 2009/0202686 A1* | 8/2009 | Lavie | B41M 3/006 |
| | | | 426/231 |
| 2009/0205747 A1* | 8/2009 | Lillard, Jr. | G07F 13/025 |
| | | | 141/94 |
| 2009/0317519 A1* | 12/2009 | Lavie | A23L 2/58 |
| | | | 426/87 |
| 2017/0066252 A1* | 3/2017 | Eliav | G06Q 30/0635 |

* cited by examiner

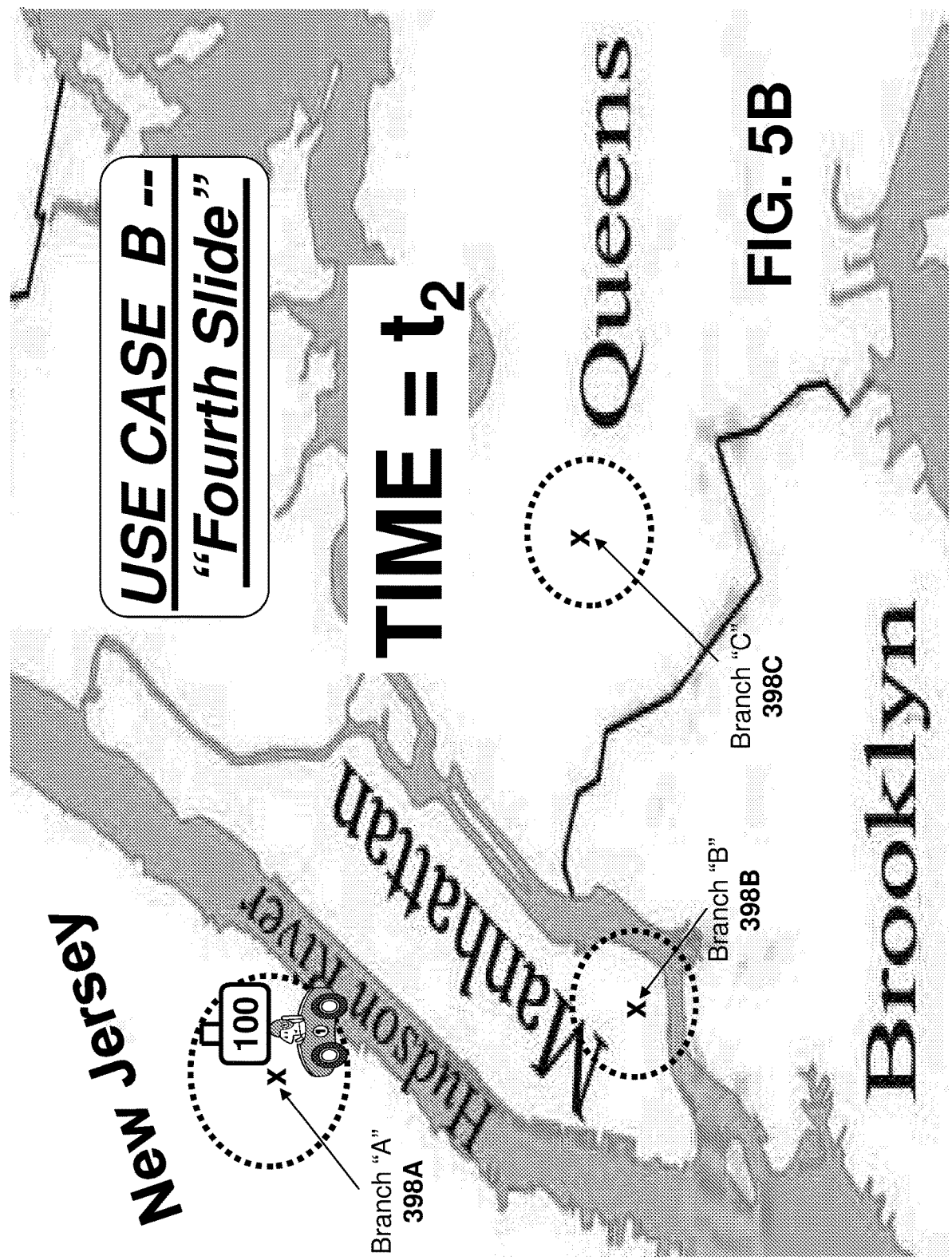

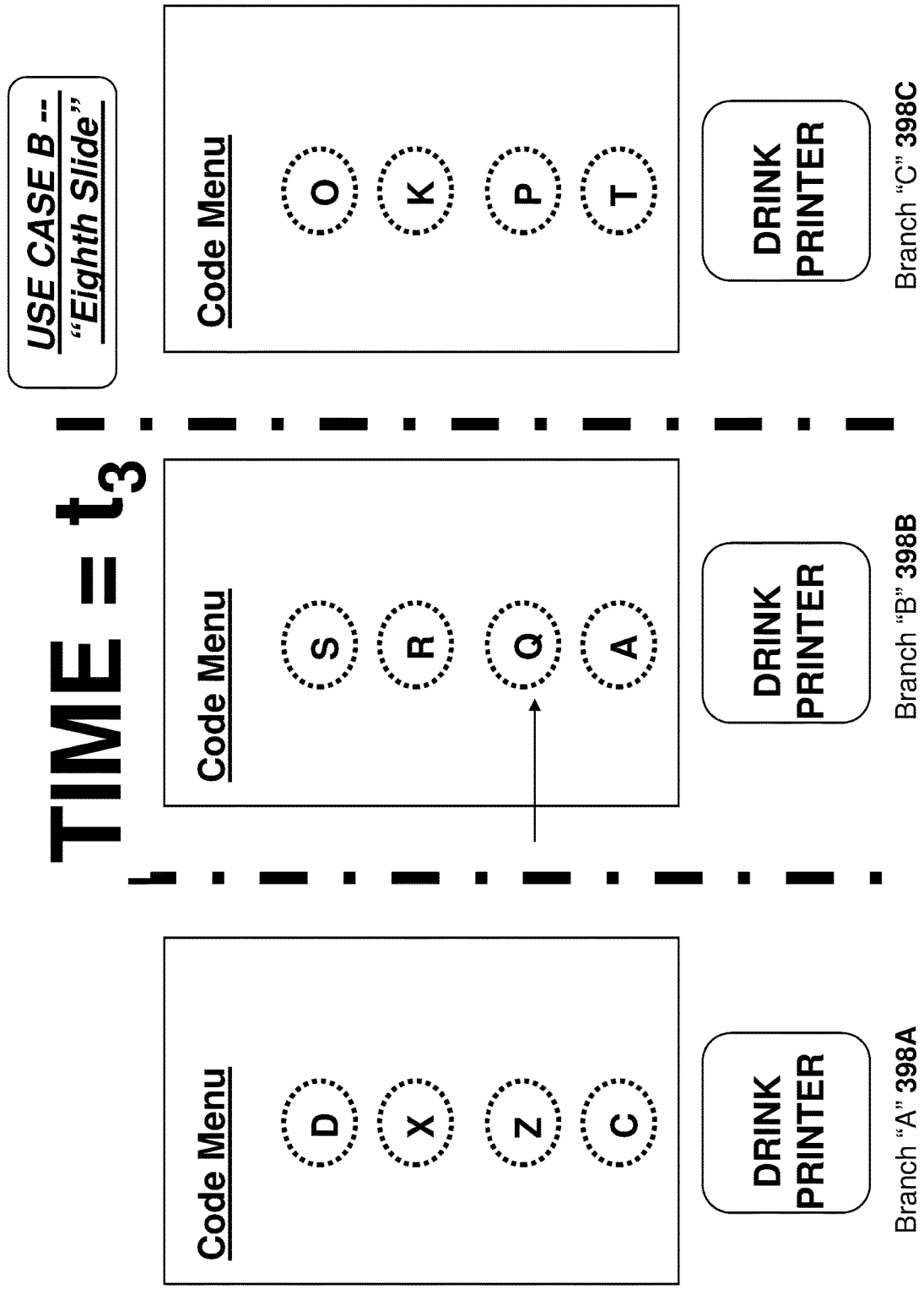

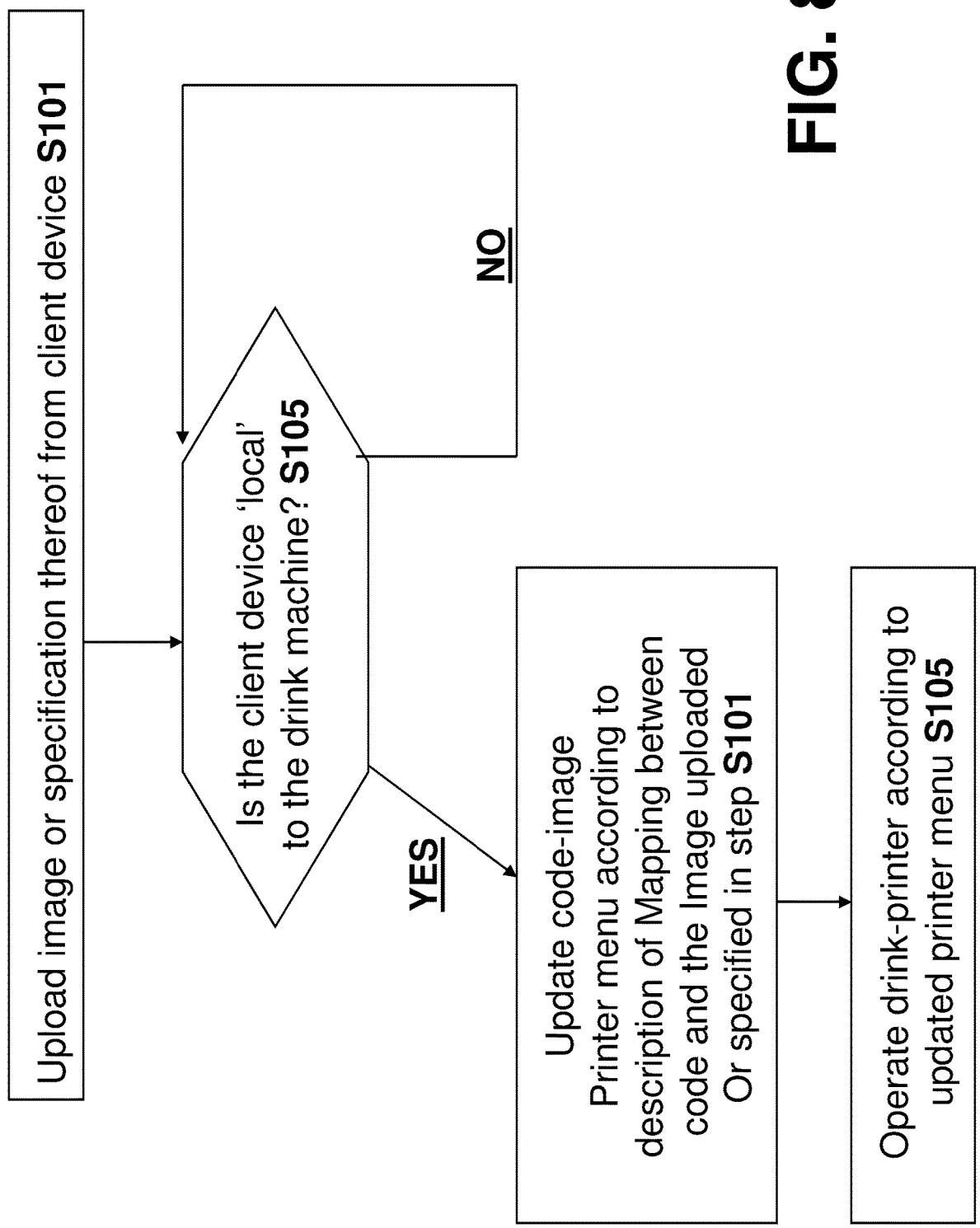

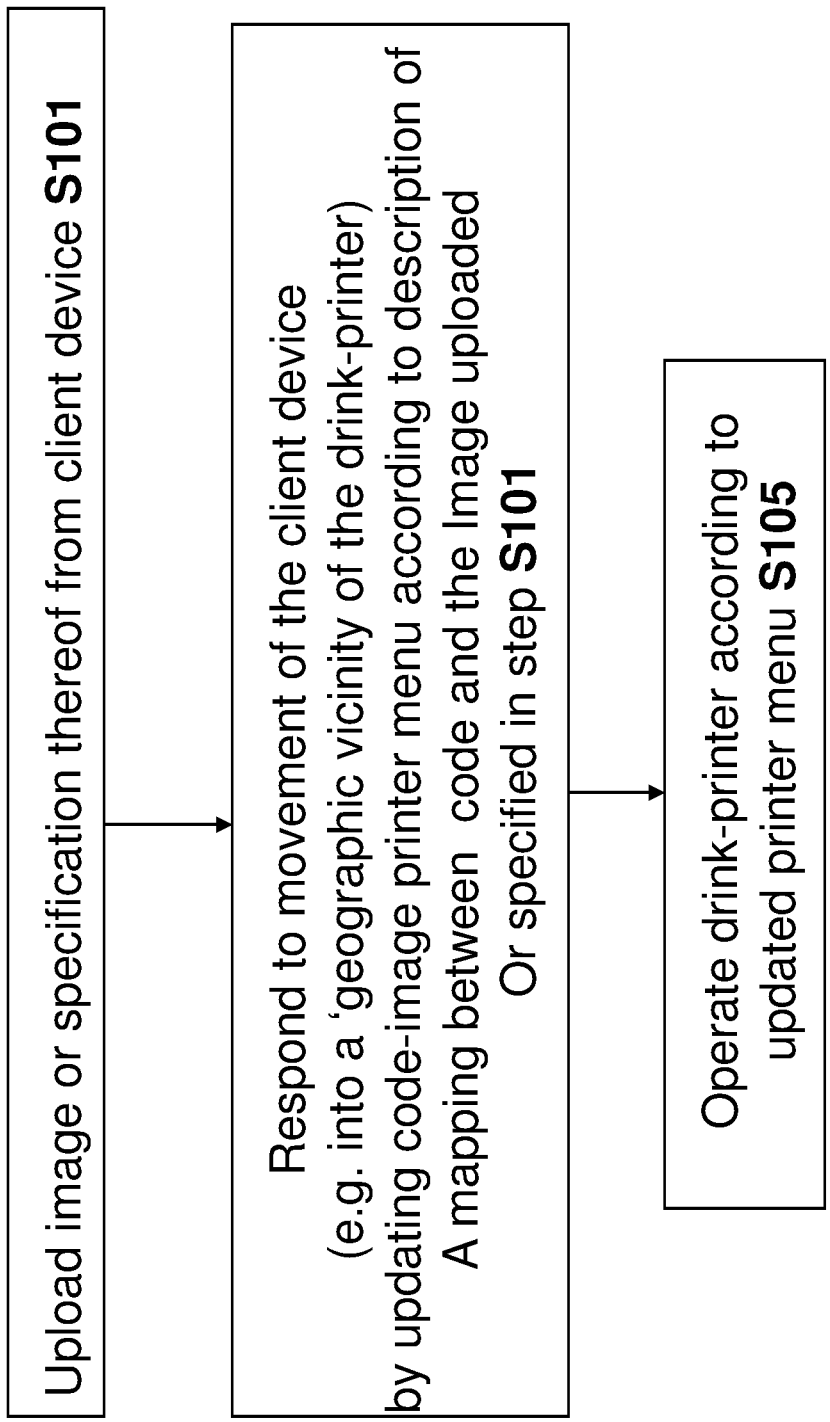

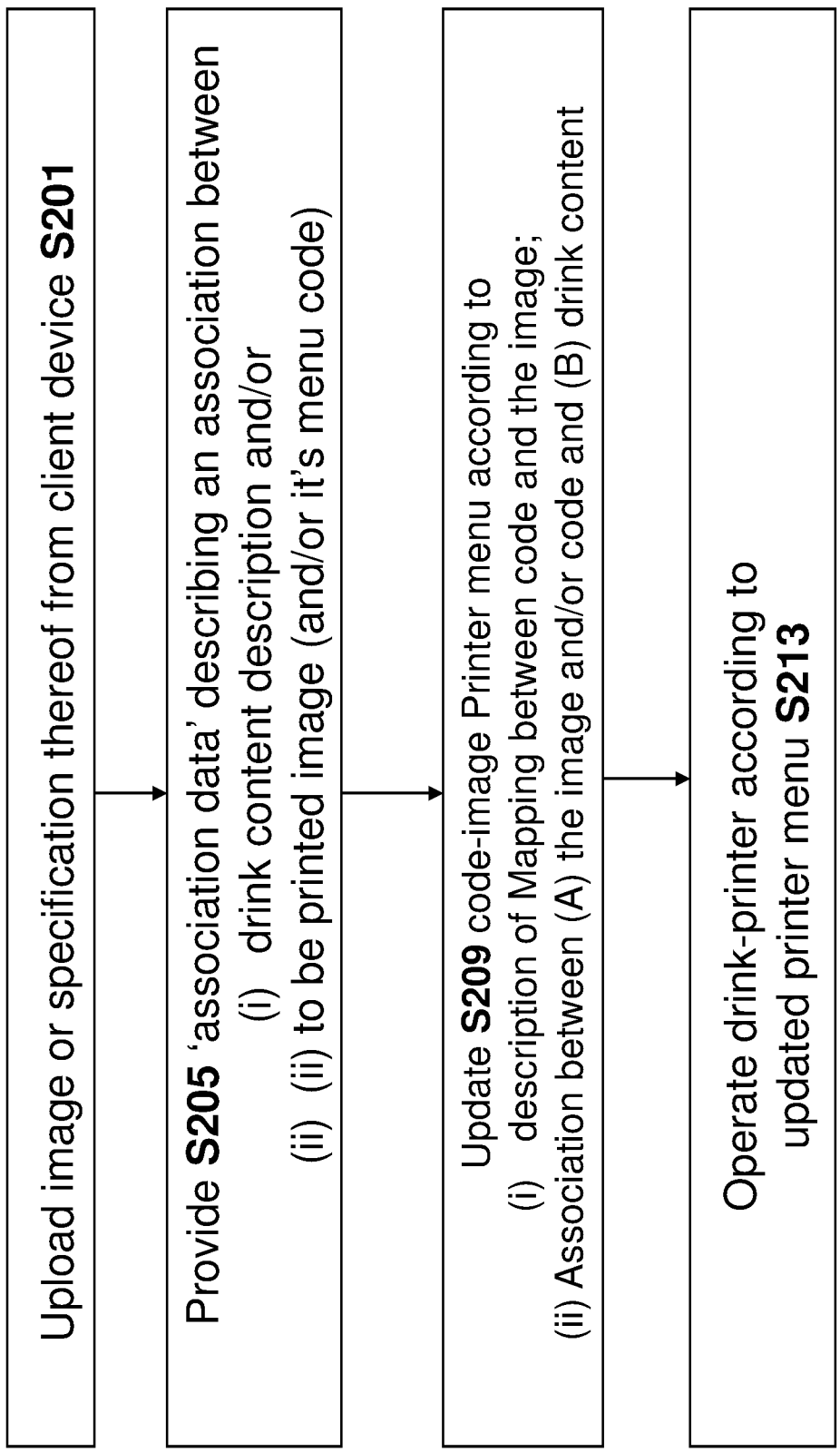

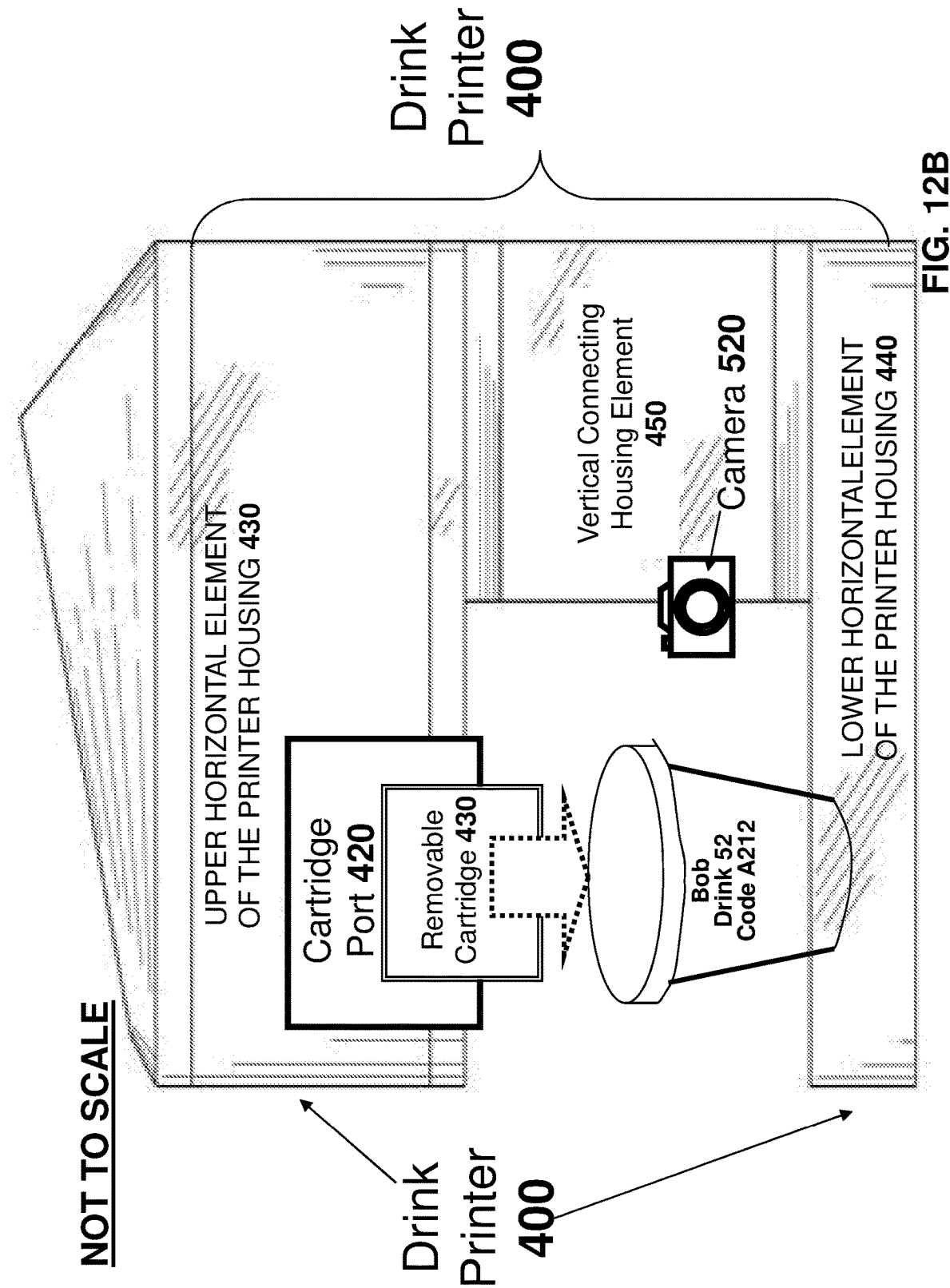

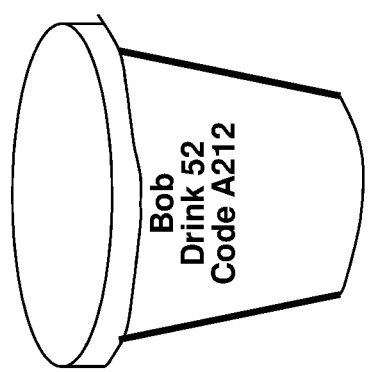
FIG. 12C

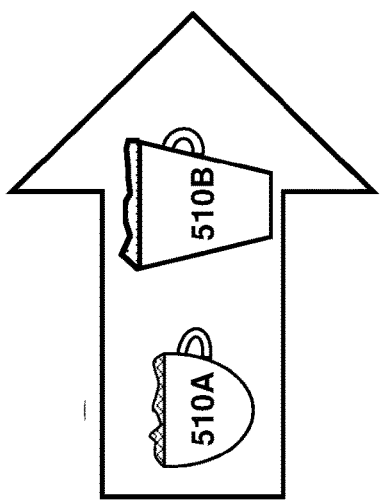
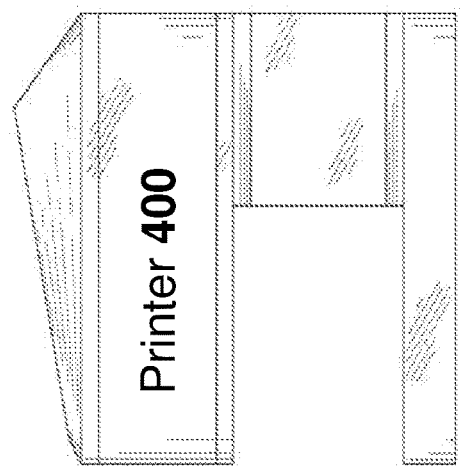
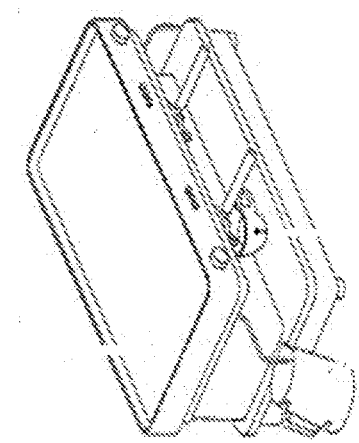
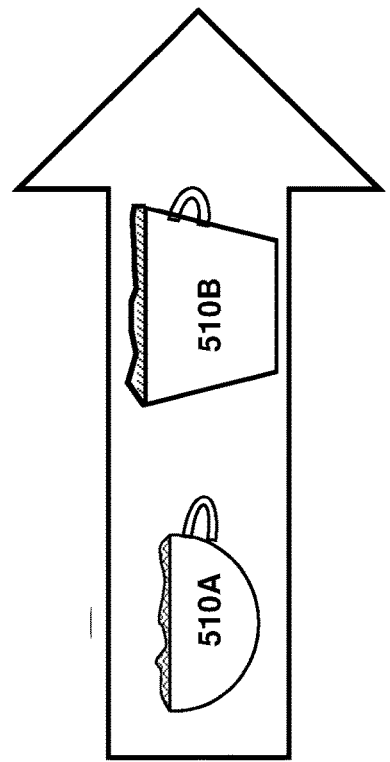
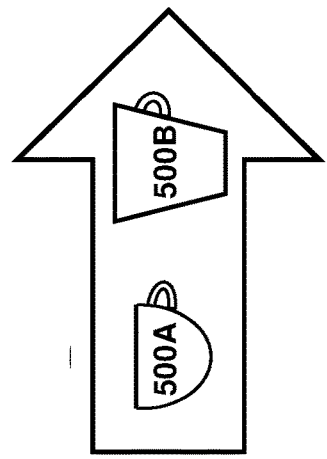
FIG. 17A

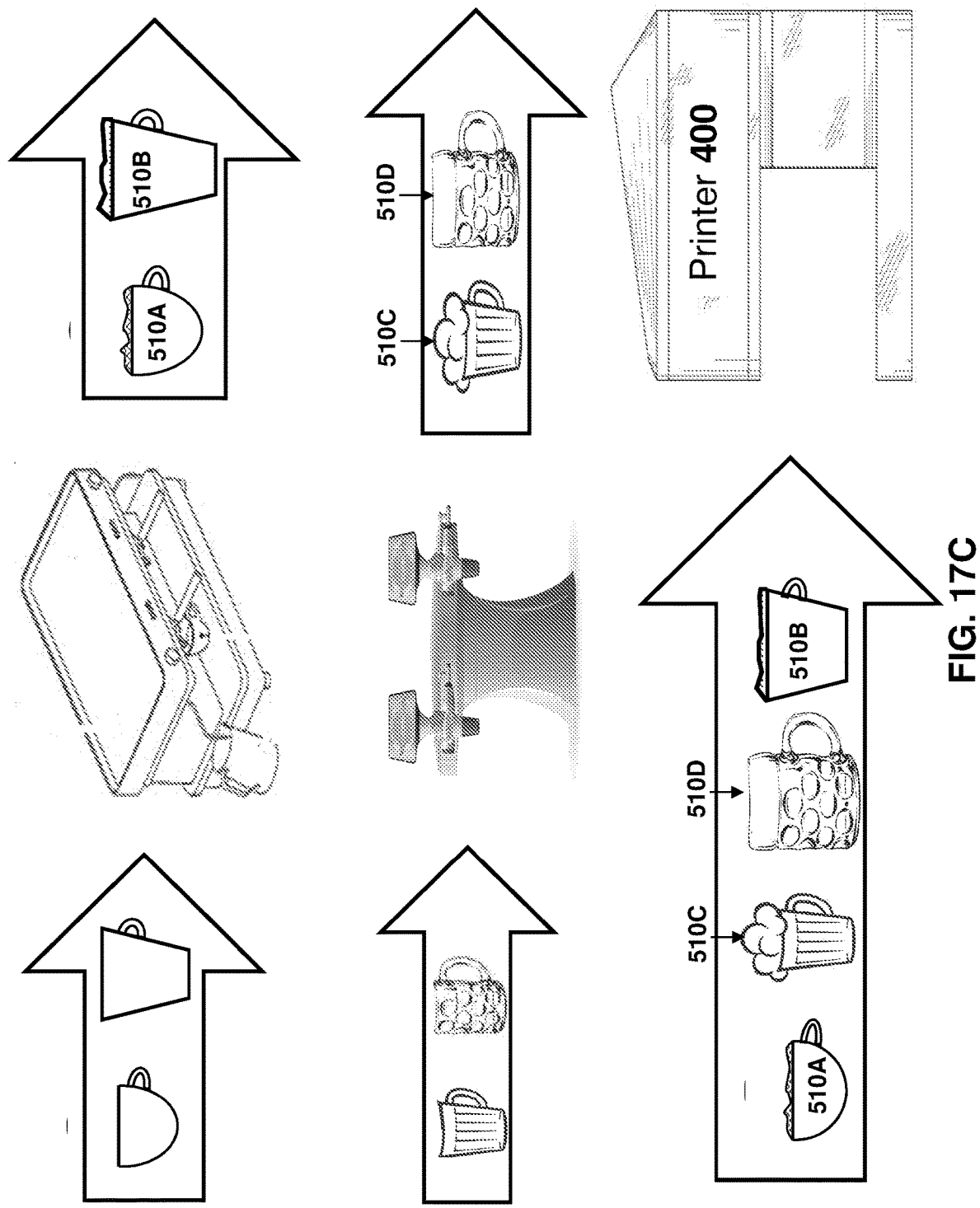

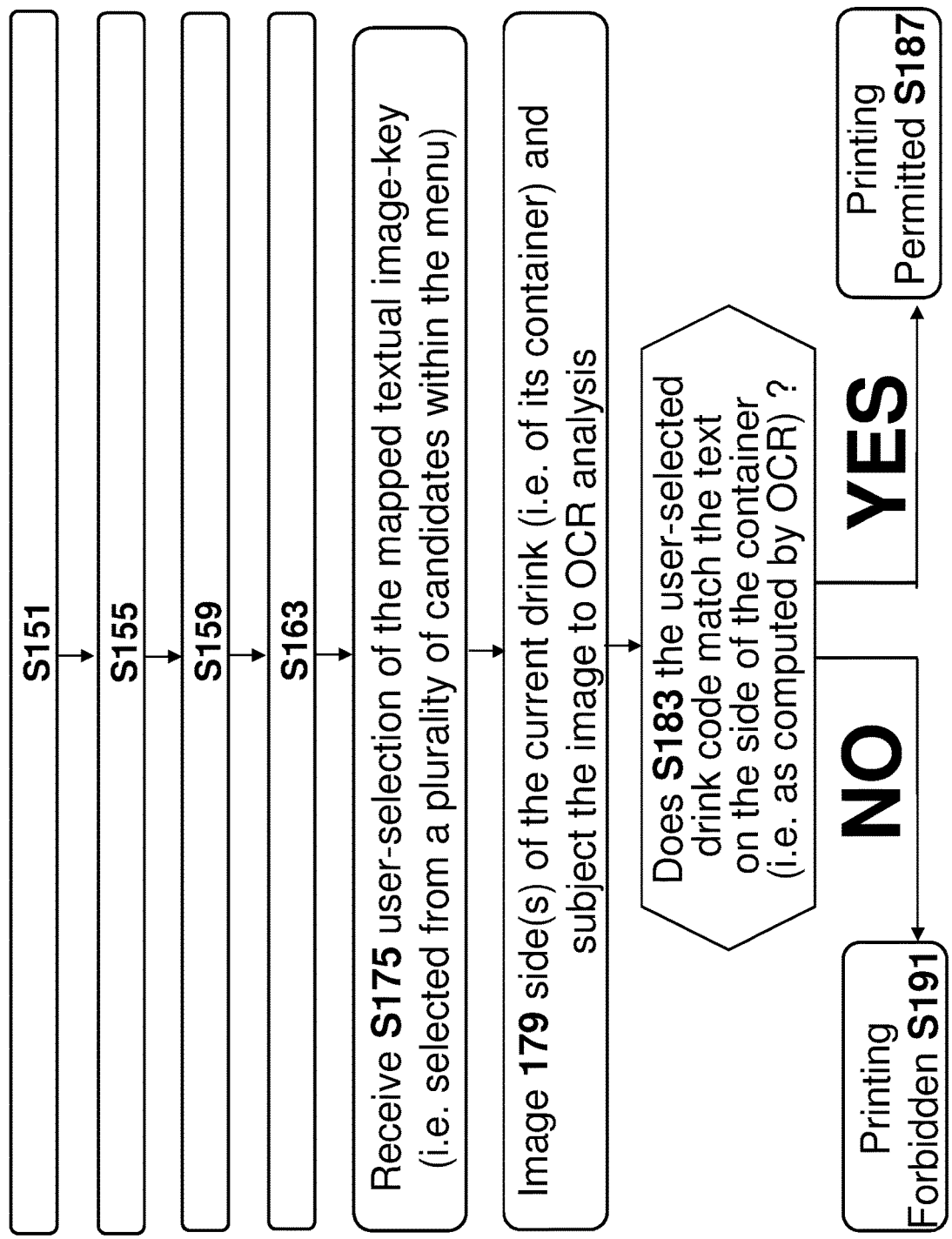

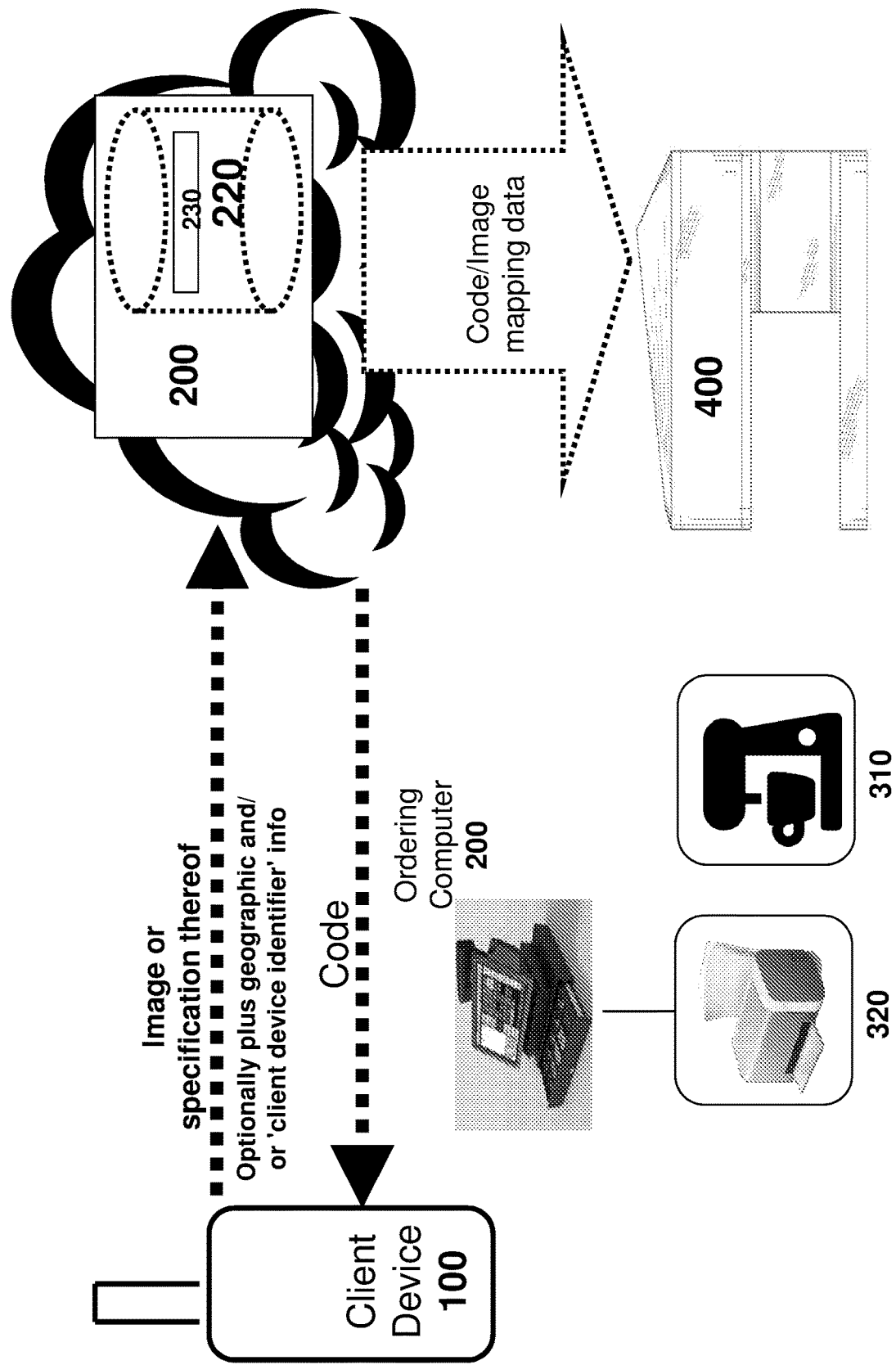

METHOD AND APPARATUS FOR PRINTING ON A DRINK

CROSS-REFERENCE TO RELATED APPLICATIONS

The present application claims priority to U.S. provisional patent application Ser. No. 62/354,093 filed on Jun. 26, 2016 which is incorporated herein by reference in its entirety. The present application is a continuation in part of U.S. non-provisional patent application Ser. No. 15/191,465 filed on Jun. 26, 2016 which is incorporated herein by reference in its entirety. U.S. non-provisional patent application Ser. No. 15/191,465 claims priority to U.S. provisional patent application Ser. No. 62/183,695 filed on Jun. 26, 2015 which is incorporated herein by reference in its entirety.

BACKGROUND

Figure 14:
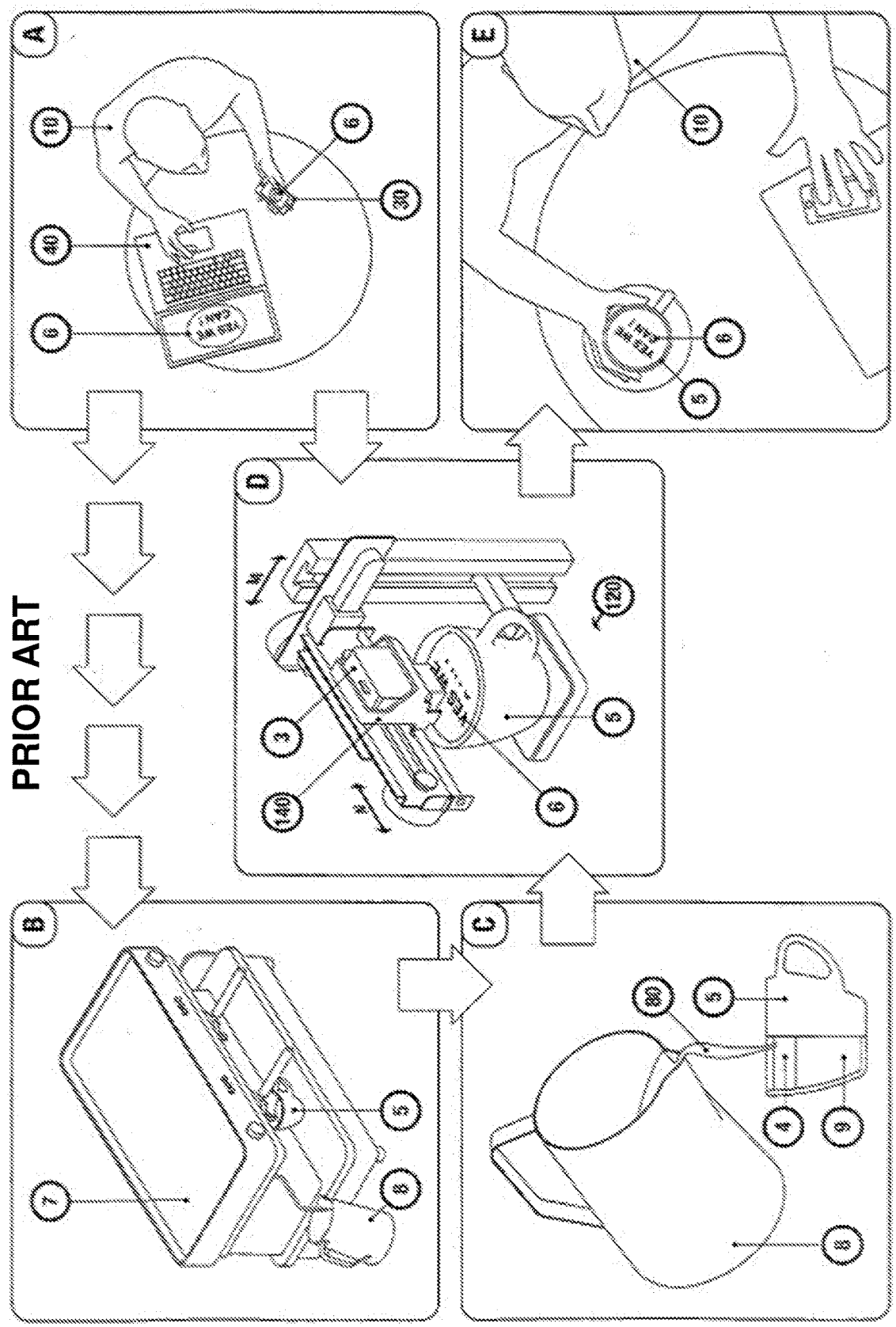

FIG. 14 (PRIOR ART) is taken from US 2009/0317519, incorporated herein by reference.

PCT/IL2006/000379, incorporated herein by reference in its entirety, discloses Optical sensor devices, image processing devices, methods and computer readable code computer-readable storage media for detecting detected from a food item such as food tissue, a consumable beverage such as an alcoholic beverage, a dairy product, wine, a baked good, a fruit and a vegetable. Exemplary parameters related to food items include but are not limited to a parameter indicative of cooking or spoilage, a pH, a concentration of an antioxidant, and a concentration of an anti-inflammatory agent.

SUMMARY OF EMBODIMENTS

A drink-printing system for printing on a current drink comprising: a. an ink-jet printer defining a target-location; b. a plurality of colorant reservoirs; c. one or more sensor(s) for sensing property-data of a current drink that is currently at the target location so as to perform at least one of the following drink-distinguishing operations for the current drink: distinguishing between a coffee and beer; distinguishing between multiple types of coffee; distinguishing between multiple types beer; d. control circuitry for: i. causing the ink-jet printer to print, on an upper surface of the current drink, a pre-stored digital image; and ii. response to output of the sensor(s), causing the ink-jet printer to dynamically select a colorant reservoir for the ink-jet printing in accordance with the results of drink-distinguishing operation(s).

In some embodiments, in response to a determining by the sensor(s) that the current drink is a coffee, the control circuitry selects a coffee-based colorant reservoir.

In some embodiments, in response to a determining by the sensor(s) that the current drink is a coffee, the control circuitry selects a hops-based colorant reservoir.

In some embodiments, in response to a determining by the sensor(s) that the current drink is a beer, the control circuitry selects a hops-based colorant reservoir.

In some embodiments, (i) a first of the colorant reservoirs is coffee based and a coffee-based ink is stored therein and (ii) a second of the colorant reservoirs is hops based and a hops-based ink is stored therein.

In some embodiments, comprising a plurality of malt-based colorant reservoirs and the control circuitry selects between them for the ink-jet printing according to the results of the distinguishing between the multiple types of beer.

In some embodiments, comprising a plurality of hops-based colorant reservoirs and the control circuitry selects between them for the ink-jet printing according to the results of the distinguishing between the multiple types of beer.

A drink-printing system for comprising: a. an ink-jet printer defining a target-location;
b. one or more sensor(s) for sensing property-data of a current drink that is currently at the target location so as to perform at least one of the following drink-identification operations for the current drink: distinguishing between a coffee and beer; distinguishing between multiple types of coffee; distinguishing between multiple types beer; c. control circuitry for responding to a detected event by causing the ink-jet printer to print a given digital image on an upper surface of the current drink, wherein the control circuitry responds to the results of drink-distinguishing operation so as to allow or forbid inkjet printing of the given digital image on the upper surface of the current drink.

In some embodiments, further comprising: d. a drink-order database describing a plurality of drink-orders, each drink-order associating drink property data with a digital image to be printed; and e. a user interface for receiving a user-specifying of the given digital image as the image to be printed, wherein if user-specified digital image is associated with a coffee within the drink order database, the control circuitry requires the sensor(s) to identify the current drink as coffee in order to allow the inkjet printing of the given digital image.

In some embodiments, further comprising: d. a drink-order database describing a plurality of drink-orders, each drink-order associating drink property data with a digital image to be printed; and e. a user interface for receiving a user-specifying of the given digital image as the image to be printed, wherein if user-specified digital image is associated with a specific type of coffee within the drink order database, the control circuitry requires the sensor(s) to identify the current drink as the specific type of coffee in order to allow the inkjet printing of the given digital image.

In some embodiments, d. a drink-order database describing a plurality of drink-orders, each drink-order associating drink property data with a digital image to be printed; and e. a user interface for receiving a user-specifying of the given digital image as the image to be printed, wherein if user-specified digital image is associated with a specific type of coffee within the drink order database, the control circuitry requires the sensor(s) to identify the current drink as the specific type of coffee in order to allow the inkjet printing of the given digital image.

In some embodiments, the sensor(s) distinguish between coffee and beer and the control circuitry dynamically selects the colorant reservoir or selectively allows or forbids the inkjet printing of the given digital image on the upper surface of the current drink according to the distinguishing between coffee and beer.

In some embodiments, the sensor(s) distinguish between multiple types of beer and the control circuitry dynamically selects the colorant reservoir or selectively allows or forbids the inkjet printing of the given digital image on the upper surface of the current drink according to the distinguishing between multiple types of beer.

In some embodiments, the sensor(s) distinguish between multiple types of coffee and the control circuitry dynamically selects the colorant reservoir or selectively allows or forbids the inkjet printing of the given digital image on the upper surface of the current drink according to the distinguishing between multiple types of coffee.

In some embodiments, the sensor comprises at least one of a color sensor, a camera, a spectrometer, a chemical concentration sensor, a vapor sensor for sensing properties of vapors above the upper surface of the current beverage, a surface texture sensor, a pH sensor, colorimeter, and a color-tone sensor.

In some embodiments, the sensor distinguishes between coffee and beer, and the control circuitry operates according to the results of the beer-coffee distinguishing.

In some embodiments, the sensor distinguishes between different types of beer, and the control circuitry operates according to the results of the beer-type distinguishing.

In some embodiments, the sensor(s) distinguishes between different types of beer by measuring an absorbance of coherent light.

In some embodiments, the sensor(s) distinguishes between different types of beer by measuring foam quality and/or property(ies).

In some embodiments, the sensor(s) distinguishes between different types of coffee roasts, and the control circuitry operates according to the results of the coffee—roast distinguishing.

In some embodiments, the distinguishing is performed according to pre-stored data descriptive of each roast color.

In some embodiments, wherein the sensor analyzes geometric properties of the beverage-container and the control circuitry operates according to the results of the beverage-container geometric-property analysis.

In some embodiments, the sensor distinguishes between a beer mug and a coffee mug based upon differing geometric properties therebetween.

In some embodiments, the sensor distinguishes between coffee and beer based upon temperature of the contents of the current beverage wherein a higher temperature indicates coffee and a lower temperature indicates beer.

A method of operating a drink-printing system, method comprising: a. providing each of the following: i. an ink-jet printer defining a target-location; ii. electronic circuitry; and iii. a plurality of colorant reservoirs; b. operating one or more one or more sensor(s) for sensing property-data of a current drink that is currently at the target location so as to perform at least one of the following drink-distinguishing operations for the current drink: i. distinguishing between a coffee and beer; ii. distinguishing between multiple types of coffee; iii. distinguishing between multiple types beer; c. operating the electronic circuitry to control the ink-jet printer as follows: i. causing the ink-jet printer to print, on an upper surface of the current drink, a pre-stored digital image; and ii. responsive to output of the sensor(s), causing the ink-jet printer to dynamically select a colorant reservoir for the ink-jet printing in accordance with the results of drink-distinguishing operation(s).

In some embodiments, in response to a determining by the sensor(s) that the current drink is a coffee, the control circuitry selects a coffee-based colorant reservoir.

In some embodiments, in response to a determining by the sensor(s) that the current drink is a coffee, the control circuitry selects a hops-based colorant reservoir.

In some embodiments, in response to a determining by the sensor(s) that the current drink is a beer, the control circuitry selects a hops-based colorant reservoir.

In some embodiments, wherein: (i) a first of the colorant reservoirs is coffee based and a coffee-based ink is stored therein and (ii) a second of the colorant reservoirs is hops based and a hops-based ink is stored therein.

In some embodiments, comprising a plurality of malt-based colorant reservoirs and the control circuitry selects between them for the ink-jet printing according to the results of the distinguishing between the multiple types of beer.

In some embodiments, comprising a plurality of hops-based colorant reservoirs and the control circuitry selects between them for the ink-jet printing according to the results of the distinguishing between the multiple types of beer.

A method of operating drink-printing system, the method comprising: a. an ink-jet printer defining a target-location; b. providing one or more sensor(s) for sensing property-data of a current drink that is currently at the target location so as to perform at least one of the following drink-identification operations for the current drink: distinguishing between a coffee and beer;
distinguishing between multiple types of coffee; distinguishing between multiple types beer; c. operating the control circuitry to respond to a detected event by causing the ink-jet printer to print a given digital image on an upper surface of the current drink, wherein the control circuitry responds to the results of drink-distinguishing operation so as to allow or forbid inkjet printing of the given digital image on the upper surface of the current drink.

In some embodiments, the sensor(s) distinguish between coffee and beer and the control circuitry dynamically selects the colorant reservoir or selectively allows or forbids the inkjet printing of the given digital image on the upper surface of the current drink according to the distinguishing between coffee and beer.

In some embodiments, the sensor(s) distinguish between multiple types of beer and the control circuitry dynamically selects the colorant reservoir or selectively allows or forbids the inkjet printing of the given digital image on the upper surface of the current drink according to the distinguishing between multiple types of beer.

In some embodiments, the sensor(s) distinguish between multiple types of coffee and the control circuitry dynamically selects the colorant reservoir or selectively allows or forbids the inkjet printing of the given digital image on the upper surface of the current drink according to the distinguishing between multiple types of coffee.

In some embodiments, the sensor comprises at least one of a color sensor, a camera, a spectrometer, a chemical concentration sensor, a vapor sensor for sensing properties of vapors above the upper surface of the current beverage, a surface texture sensor, a pH sensor, colorimeter, and a color-tone sensor.

In some embodiments, the sensor distinguishes between coffee and beer, and the control circuitry operates according to the results of the beer-coffee distinguishing.

In some embodiments, the sensor distinguishes between different types of beer, and the control circuitry operates according to the results of the beer-type distinguishing.

In some embodiments, the sensor(s) distinguishes between different types of beer by measuring an absorbance of coherent light.

In some embodiments, the sensor(s) distinguishes between different types of beer by measuring foam quality and/or property(ies).

In some embodiments, the sensor distinguishes between different types of coffee roasts, and the control circuitry operates according to the results of the coffee—roast distinguishing.

A drink-printing system for comprising: a. an ink-jet printer defining a target-location; b. one or more camera(s) for imaging a current drink that is currently at the target location so as to generate a camera-acquired digital image; c. an optical character recognition (OCR) module for subjecting, to an OCR analysis, the camera-acquired digital image and/or a derivative thereof, so as to determine a sequence of characters appearing on the container; d. control circuitry for responding to a detected event by causing the ink-jet printer to print a given digital image on an upper surface of the current drink, wherein the control circuitry responds to the results of OCR analysis so as to allow or forbid inkjet printing of the given digital image on the upper surface of the current drink.

In some embodiments, further comprising: analysis circuitry for computing a relation between sequence of characters and the given digital image, wherein the control circuitry allows or forbids the inkjet printing in response to the output of the analysis circuitry and according to the computed relation between: the OCR-determined sequence of characters; and the digital image.

A drink-printing system comprising: a. an ink-jet printer defining a target-location; b. one or more camera(s) for imaging a current drink that is currently at the target location so as to generate a camera-acquired digital image; c. an optical character recognition (OCR) module for subjecting, to an OCR analysis, the camera-acquired digital image and/or a derivative thereof, so as to determine a sequence of characters appearing on the container; d. a mapped drink-code database for storing a mapping between (i) a plurality of drink codes and (ii) a respective pre-stored digital print-image; e. a user interface for displaying a menu of the drink codes and for receiving a user-selection of one of the menu-displayed drink-codes; f. control circuitry for responding to a detected event by causing the ink-jet printer to print, on an upper surface of the current drink, the pre-stored digital image that is mapped to the user-selected drink-code within the mapped drink-code database; and g. text-processing circuitry for computing a relationship between the user-selected drink-code and the OCR-module-determined sequence of characters; and wherein the control circuitry allows or forbids the inkjet printing according to a computed relation between: the OCR-determined sequence of characters; and the digital image.

In some embodiments, the relation between the user-selected drink-code and the OCR-module-determined sequence of characters is a text-match relation.

In some embodiments, i. the system further comprising a code server for responding to an upload of a digital image from a client device by updating the mapped drink-code database so as to associate the uploaded digital image with one of the drink codes; ii. the relation between the user-selected drink-code and the OCR-module-determined sequence of characters is a relation between: an identifier of the client device or of a user thereof; and the OCR-module-determined sequence of characters.

A drink-printing system for printing on a current drink comprising: a. an ink-jet printer defining a target-location; b. one or more sensor(s) for sensing property-data of a current drink that is currently at the target location, the property data describing property(ies) of contents and/or the container of the current drink; d. a mapped drink-code database for (i) storing a plurality of drink codes and (ii) mapping each drink code to: a respective pre-stored digital image; respective pre-stored drink property-data; e. a user interface for displaying a menu of candidate drink codes; and f. control circuitry for responding to a detected event by causing the ink-jet printer to print, on an upper surface of the current drink, the pre-stored digital image that is mapped to the user-selected drink-code within the mapped drink-code database, wherein the control circuitry allows or forbids the inkjet printing according to a match between: A. the sensed property-data of the current drink; and B. pre-stored drink property-data that is mapped, within the drink-code database, to the user-selected drink-code.

A method of providing a customized drink, the method comprising: a. maintaining, in computer memory, a code-image map between drink-codes and digital graphical images; b. in response to an uploading of a digital graphical image, updating the code-image map to include a mapping between the uploaded digital graphical image and a given drink-code; c. causing a multi-code menu of a user-interface to display the given drink-code, the user-interface being mechanically associated with an inkjet-based drink-printing machine and/or in local electronic communication therewith; and d. when a current drink is disposed beneath ink-jet nozzles of the inkjet-based drink-printing machine, responding to a user-selection of the given drink-code by causing the drink-printing machine to ink-jet print, on an upper surface of the current drink, the digital image that is mapped, to the user-selected drink-code, within the mapped drink-code database.

In some embodiments, the digital graphical image is uploaded from a client terminal, and in response to the image-uploading, the given drink-code is sent to the client terminal.

In some embodiments, the multi-code menu displays the given drink-code in response to at least one of: (i) a geographic proximity between the client terminal and the drink-printing machine; (ii) a reading of data from the client-device, the read data including one of: (i) the given drink code; and (ii) data associated with the given drink code within a digital computer in communication with an electronic device hosting the multi-code menu.

In some embodiments, the drink-code is generated in response to the uploading of the digital graphical image.

In some embodiments, the drink-printing machine prints the digital graphical image on a foamed or frothed surface of a beverage selected from the group consisting of a beer and a coffee.

In some embodiments, i. the method further comprises: before printing on the upper surface of the current drink: A. optically imaging a container of the current drink; B. subjecting an electronic representation of the optically-imaged container to OCR-analysis so as to determine characters appearing on the container of the current drink; and ii. the drink-printing machine automatically responds to the responds to the results of the OCR-analysis so as to allow or forbid inkjet printing of the given digital image on the upper surface of the current drink.

In some embodiments, i. the method further comprises: before printing on the upper surface of the current drink: A. employing a sensor to sense property-data of the current drink; B. analyzing the property data; and ii. the drink-printing machine automatically responds to the responds to the results of the analyzing so as to allow or forbid inkjet printing of the given digital image on the upper surface of the current drink.

A drink-printing system for comprising: a. an ink-jet printer defining a target-location; b. one or more camera(s) for imaging a current drink that is currently at the target location so as to generate a camera-acquired digital image; c. an optical character recognition (OCR) module for subjecting, to an OCR analysis, the camera-acquired digital image and/or a derivative thereof, so as to determine a sequence of characters appearing on the container; d. control circuitry for responding to a detected event by causing the ink-jet printer to print a given digital image on an upper surface of the current drink, wherein the control circuitry responds to the results of OCR analysis so as to allow or forbid inkjet printing of the given digital image on the upper surface of the current drink.

In some embodiments, further comprising: analysis circuitry for computing a relation between sequence of characters and the given digital image, wherein the control circuitry allows or forbids the inkjet printing in response to the output of the analysis circuitry and according to the computed relation between: the OCR-determined sequence of characters; and the digital image.

A drink-printing system comprising: a. an ink-jet printer defining a target-location; b. one or more camera(s) for imaging a current drink that is currently at the target location so as to generate a camera-acquired digital image; c. an optical character recognition (OCR) module for subjecting, to an OCR analysis, the camera-acquired digital image and/or a derivative thereof, so as to determine a sequence of characters appearing on the container; d. a mapped drink-code database for storing a mapping between (i) a plurality of drink codes and (ii) a respective pre-stored digital print-image; e. a user interface for displaying a menu of the drink codes and for receiving a user-selection of one of the menu-displayed drink-codes; f. control circuitry for responding to a detected event by causing the ink-jet printer to print, on an upper surface of the current drink, the pre-stored digital image that is mapped to the user-selected drink-code within the mapped drink-code database; and g. text-processing circuitry for computing a relationship between the user-selected drink-code and the OCR-module-determined sequence of characters; and wherein the control circuitry allows or forbids the inkjet printing according to a computed relation between: the OCR-determined sequence of characters; and the digital image.

In some embodiments, the relation between the user-selected drink-code and the OCR-module-determined sequence of characters is a text-match relation.

In some embodiments, wherein: i. the system further comprising a code server for responding to an upload of a digital image from a client device by updating the mapped drink-code database so as to associate the uploaded digital image with one of the drink codes; ii. the relation between the user-selected drink-code and the OCR-module-determined sequence of characters is a relation between: an identifier of the client device or of a user thereof; and the OCR-module-determined sequence of characters A printing device for printing on a current drink comprising: a. a tray upon which the current drink rests; b. an ink-jet printer to downwardly ink-jet droplets of ink towards the tray to print an image on the drink supported by the tray; c. a display-screen; d. one or more sensor(s) for acquiring current-drink property-data describing the current drink currently supported by the tray; e. a mapped drink-code database specifying a map for a plurality of drink-printing codes, between: i. each displayed drink-printing code of the plurality of drink-printing codes; and ii. a respective combination of (i) a respective drink-printing-code-specific target-image to be printed by the ink-jet printer; and (ii) respective drink-printing-code-specific target-drink property-data describing contents of a respective target-drink and/or its container; f. analysis circuitry for computing a drink-match parameter between: i. property-data of the current drink sensed by the sensor(s) and ii. property-data of one or more of the target drinks specified by the database; g. a user-interface for: i. displaying a drink-property-heterogeneous menu comprising the plurality of drink-printing codes on the display-screen; and ii. receiving a user-selection of one of the drink codes to thereby user-specify, according to the mapped drink-code database, a target-image and target-drink property-data; h. a device controller for responding to the user drink-code selection, in accordance with content of the mapped drink-code database, output of the sensor(s) and output of the analysis circuitry, by printing the user-interface-specified target-image onto an upper surface of the current drink in a manner that is contingent upon the drink-match parameter that is specific to the combination of: i. the user-specified target-drink property-data as specified via the user-interface; ii. the current drink property-data as sensed by the sensor(s).

In some embodiments, the sensor is an image sensor configured to acquire a digital image of an outer wall of a container of the current drink resting on the tray.

In some embodiments, the analysis circuitry is configured to subject the acquired digital image to optical-character-recognition (OCR) analysis derive therefrom the target-drink property-data.

A printing device for printing on a current drink comprising: a. a tray upon which the current drink rests; b. an ink-jet printer to downwardly ink-jet droplets of ink towards the tray to print an image on the drink supported by the tray; c. a display-screen; d. a mapped drink-code database specifying a map for a plurality of drink-printing codes, between: i. each displayed drink-printing code of the plurality of drink-printing codes; and ii. a respective combination of (i) a respective drink-printing-code-specific target-image to be printed by the ink-jet printer; and (ii) respective drink-printing-code-specific target-drink property-data describing a contents of respective target-drink and/or its container; e. a user-interface for: i. displaying a menu comprising the plurality of drink-printing codes drink-property-heterogeneous on the display-screen such that each drink code is displayed in a manner specific to the respective target-drink property-data associated therewith; and ii. receiving a user-selection of one of the drink codes to thereby user-specify, according to the mapped drink-code database, a target-image; f. a device controller for responding to the user drink-code selection, in accordance with content of the mapped drink-code database, output of the sensor(s) and output of the analysis circuitry, by printing the user-interface-specified target-image onto an upper surface of the current drink.

A method of providing a customized drink by a plurality of drink-manufacturing machines, each drink-manufacturing machine deployed at a different respective location and including and/or being locally coupled to a different respective display-screen, the method comprising: a. maintaining, in computer memory, a code-image map between code image-keys and digital graphical images b. in response to an uploading from a user-terminal, of a digital graphical image or a specification thereof: A. updating the code-image map to include a mapping between (i) a code-image key specific to the digital graphical image and (ii) uploaded digital graphical image of specification thereof and optionally an identifier of the user-terminal; and B. sending the code image key to the user terminal; c. monitoring a location of the user-terminal; d. in accordance with the results of the monitoring, sending menu-command information to each of the drink-manufacturing machines to regulate the contents of a code-menu on each of the drink-manufacturing-machine-local screens such that: i. in response to a decrease in a distance between given one of the user terminals and a given one of the drink-manufacturing machines, adding or promoting a code image-key resident in the user terminal to or within a menu of the given one of drink-manufacturing machines; and ii. in response to an increase in a distance between given one of the user terminals and a given one of the drink-manufacturing machines, removing or demoting a code image-key resident in the user terminal from or within a menu of the given one of drink-manufacturing machines; and e. for each of the drink manufacturing machines, in response to a user-selection of one of the drink codes, printing on a drink its associated a target-image as defined by the a code-image map.

A method of providing a customized drink, the method comprising: a. maintaining, in computer memory, a text-image map between textual image-keys and digital graphical images; b. in response to an uploading of a digital graphical image, updating the text-image map to include a mapping between the uploaded digital graphical image and a machine-generated textual image-key for the uploaded graphical image; c. receiving, via user-input device of an order-generating computer-terminal, both a drink description and a user-supplied textual image-key; d. electronically sending, from the order-generating computer-terminal to one or more production machines of a drink-production machine-array, a text-hybrid of the (i) a drink text-code matching the drink description and (ii) the user-supplied textual image-key; e. visually displaying. on a display-screen of one or more drink-production machines, the text-hybrid; f. responding to a user input: (i) to one or more of the drink-production machines and (ii) of data matching the drink-text-code of the textual-hybrid, by electronically generating a drink that matches the drink-text-code; and g. responding to a user input (i) to one or more of the drink-production machines and (ii) of data matching the user-supplied textual image-key of the textual hybrid, by printing on the drink and in edible-media, the digital graphical image that matches, according to the text-image map, the user-supplied textual image-key.

A printing device for printing on a current drink comprising: a. an ink-jet printer defining a target-location; b. one or more sensor(s) for sensing property-data of a current drink that is currently at the target location, the property data describing property(ies) of contents and/or the container of the current drink; d. a mapped drink-code database for (i) storing a plurality of drink codes and (ii) mapping each drink code to: a respective pre-stored digital image; respective pre-stored drink property-data; e. a user interface for displaying a menu of candidate drink codes; and f. control circuitry for responding to a user-selection of one of the displayed candidate drink codes by triggering a print operation to cause the ink-jet printer to print, on an upper surface of the current drink, the pre-stored digital image that is mapped to the user-selected drink-code within the mapped drink-code database; and g. analysis circuitry for determining if there is a match between (i) the sensed property-data of the current drink; and (ii) pre-stored drink property-data that is mapped, within the drink-code database, to the user-selected drink-code, wherein the control circuitry responds to output of the analysis circuitry by requiring the match in order to trigger the print operation.

A printing device for printing on a current drink comprising: a. an ink-jet printer defining a target-location; b. one or more camera(s) for imaging at least a portion of container of a current drink that is currently at the target location so as to generate a camera-acquired digital image; c. an OCR module for analyzing at least one of: i. the camera-acquired digital image; and ii. a derivative thereof, so as to determine a sequence of characters appearing the container; d. a mapped drink-code database for storing a mapping between (i) a plurality of drink codes and (ii) pre-stored digital print-images; e. a user interface for displaying a menu of the drink codes; and f. control circuitry for responding to a user-selection of one of the menu-displayed drink codes, only if the selected drink-code matches the sequence of characters, by causing the ink-jet printer to print, on an upper surface of the current drink, the pre-stored digital print-image mapped to the user-selected drink-code.

A printing device for printing on a current drink comprising: a. an ink-jet printer defining a target-location; b. one or more sensor(s) for sensing property-data of a current drink that is currently at the target location, the property data describing property(ies) of contents and/or the container of the current drink; d. a mapped drink-code database for (i) storing a plurality of drink codes and (ii) mapping each drink code to: a respective pre-stored digital image; respective pre-stored drink property-data; e. a user interface for displaying a menu of candidate drink codes; and f. control circuitry for responding to a user-selection of one of the displayed candidate drink codes by causing the ink-jet printer to print, on an upper surface of the current drink, the pre-stored digital image that is mapped to the user-selected drink-code within the mapped drink-code database; and g. analysis circuitry for determining if there is a match between (i) the sensed property-data of the current drink; and (ii) pre-stored drink property-data that is mapped, within the drink-code database, to the user-selected drink-code, wherein the control circuitry responds to output of the analysis circuitry so that a positive determining by the analysis circuitry is required for the control circuitry to cause the ink-jet printer to print, on the upper surface of the current drink, the pre-stored digital image that is mapped to the user-selected drink-code.

A printing device for printing on a current drink comprising: a. an ink-jet printer defining a target-location; b. a mapped drink-code database for storing (i) storing a plurality of drink codes and (ii) a mapping of each drink code to: a respective pre-stored digital image; and respective pre-stored drink property-data, the property data describing property(ies) of contents and/or a container of a candidate drink; c. a user interface for displaying a menu of candidate drink codes such that each drink code is displayed in a manner specific to the respective pre-stored drink property-data mapped thereto in the mapped drink-code database; and d. control circuitry for responding to a user-selection of one of the displayed candidate drink codes by causing the ink-jet printer to print, on an upper surface of the current drink, the pre-stored digital image that is mapped to the user-selected drink-code within the mapped drink-code database.

A printing device for printing on a current drink comprising: a. an ink-jet printer defining a target-location; b. a mapped drink-code database for storing (i) storing a plurality of drink codes and (ii) a mapping of each drink code to: a respective pre-stored digital image; and respective pre-stored drink property-data, the property data describing property(ies) of contents and/or a container of a candidate drink; c. a user interface for displaying a menu of candidate drink codes such that each drink code is displayed in a manner specific to the respective pre-stored drink property-data mapped thereto in the mapped drink-code database; and d. control circuitry for responding to a user-selection of one of the displayed candidate drink codes by causing the ink-jet printer to print, on an upper surface of the current drink, the pre-stored digital image that is mapped to the user-selected drink-code within the mapped drink-code database.

BRIEF DESCRIPTION

FIGS. 1B, 2, 9A-9B, 10, 12A-12C describe a drink printing system or portions thereof.
FIGS. 3, 4, 5A-5C, 6A-6C describe use case B.
FIGS. 7A-7D describe used case C.

FIGS. 8A-8B, 11 and 13A-13B are flow charts of methods according to some embodiments of the invention.

FIGS. 14-16, 17A-17C, 18A-18C, 19A-19C and 20 describe additional examples.

DETAILED DESCRIPTION

Definitions

Within this application the following terms should be understood to have the following meaning:

A) drink—contents (i.e. including a fluid) within a container, preferably having an upper surface that is foamed and/or frothed. The term 'drink' or 'beverage' are used interchangeably. Examples of 'drinks' or 'beverages' include but are not limited to (i) 'coffee' and variations thereof (e.g. cappuccino) and (ii) beer. The container may have a generally cylindrical form-factor and may be, for example, a 'cup' or a 'glass.' A 'drink' includes both (i) contents of the drink and/or (ii) a container in which the material resides. A 'size' of the drink may relate to any combination of (i) a 'height' of the drink' or (ii) a measure of a rim of the container—.e.g. a circumference or a diameter or a radius.

B) drink-printing machine'—a machine including an ink-jet printer and configured to print designs (e.g. including photographs or other graphics) onto an upper surface of a drink. In some embodiments, the drink-printing machine includes a reservoir of edible ink—e.g. coffee-based (e.g. for printing on coffee-based beverages) or malt-based (e.g. for printing on beer). As is known in the art of ink-jet printing, the drink-printing machine C) 'electronic circuitry' or 'circuitry'—any hardware (e.g. digital and/or analog electronics), or software or combinations thereof. In some embodiments, 'circuitry' includes a digital computer. "Analysis circuitry" is electronic circuitry configured to perform a data-analysis function. "Memory" or 'storage" (used interchangably) refers to volatile (e.g. RAM) and/or non-volatile (e.g. flash or magnetic medium) computer storage. "Circuitry" or 'memory" may be local to a given device (or locally-coupled devices) or may be non-locally distributed.

D) A device controller—any combination of electronic components, software components and/or mechanical components required to perform a function—e.g. to cause an ink-jet printer to print a specific pattern on an upper surface of a specific drink.

E) a drink-generating machine—a machine for providing a drink within a container. For example, the drink-generating machine may be a simple dispenser or may be configured to dispense multiple ingredients at relative quantities or at specific temperatures. In some embodiments, a drink-generating machine may include a frother or may be configured to agitate liquids to form (or modify) bubbles and/or foams thereform.

F) A drink production machine is either a 'drink-generating machine' or a 'drink-printing machine" or a hybrid therebetween. A 'hybrid' may be a single machine configured to both 'provide' (e.g. generate) the drink and to print on an upper surface of the drink.

G) a 'machine-user'—this is a user of a drink-production machine—e.g. a barista. The 'machine-user' is not required to be the same person as the end-customer (i.e. who will consume the drink). Unless specified otherwise (or clear otherwise from the context), a 'user' refers to a 'machine-user.'

H) user-terminal—a digital computer device operated by a user—typically having an input device (e.g. keyboard or touch-screen) a display screen and a communication module (e.g. WiFi or cellular). One example of a 'user-terminal' is a mobile phone—e.g. a cell phone.

I) a 'code' or 'drink code' or 'drink-code'—a series of symbols—e.g. displayed horizontally in spatial sequence. One example of a 'code' is a 'textual code' (e.g. comprising letters and/or calligraphy (e.g. Chinese or Japanaese or Korean) characters for far-Eastern languages) and/or numbers and/or punctuation symbols. However, the code may also include emoticons or other symbols.

As discussed below, the drink-code may explicitly appear on a user interface and a user engagement of the drink-code may thus specify the image that the user wishes to print.

Wikipedia defines "Alphanumeric" as a combination of alphabetic and numeric characters, and is used to describe the collection of Latin letters and Arabic digits or a text constructed from this collection. The term "alphanumeric" may often additionally refer to other symbols, such as punctuation and mathematical symbols. The terms "alpha-numerical' and 'textual' are used interchangably.

In embodiments, a 'code' or 'drink code' is an alphanumeric drink code, either excluding or including punctuation, either excluding or including mathematical symbols.

A plurality of codes may be presented in a user interface (e.g. as a menu of codes) and user-engagement of one of the codes causes the printing on a drink upper-surface of an associated or mapped image. In this manner, a code functions as a 'key' for the mapped image. Thus, if a code may function as an 'image key'.

J) a subset—as is known in mathematics, a set is a subset of itself. If the 'subset' does not include all elements of the set, the 'subset' is a 'proper subset.' For the present document, a null set (or empty set) is not considered a 'subset.' A 'plurality of items' is one example of a 'set' of items.

K) 'Drink printing machines' typically include a platform (e.g. a tray) where one or more drinks may be placed. For example, this tray may be operatively coupled to an elevator for raising or lowering the tray—e.g. towards a print-head of an ink-jet printer. A 'current drink' is a drink in a position to have a design printed on an upper surface of the drink—e.g. a drink within a container resting on an elevatable tray of a drink printing machine.

L) "User interface" In some embodiments, a drink printing machine includes a 'user interface' (e.g. GUI) operative to receive user input and to print a pattern onto a drink in response to the user input. For example, there may be a plurality of 'candidate patterns' or 'candidate images' that could be printed onto drinks—e.g. stored in memory of the drink. In response to and based upon input received by a user via the user interface, the drink machine may print a selected one of the patterns or images upon a surface of a 'current drink.'

As mentioned above, the drink-codes may explicitly appear on a user interface and a user engagement of the drink-code may thus specify the image that the user wishes to print. For example, the drink print machine may include and/or be operatively linked to a user interface for selecting a one of the patterns (e.g. images or photographs to print)—e.g. a menu of drink codes may be displayed and the user may select one of the codes.

The drink-code may be associated (e.g. in some sort of map or data-structure) with an image to print—thus, by selecting a 'drink code' the user implicitly selects or 'specifies' an image to print.

M) "Target" (e.g. 'target image' or 'target drink')—When a user selects an image to print, this is a 'target image.' In some embodiments, the target image may be associated (i.e.

in computer storage) with meta-data describing the 'target drink' to which the 'target image' is to be printed. For example, at some point a customer and/or user and/or machine and/or any other entity may specify "Print abc.jpeg to a large cappuccino." In this case, the 'target image' is acb.jpeg and 'large cappuccino' is the target drink. In this example, if a 'target image' is associated with the 'large cappuccino' metadata then when the user 'specifies' (e.g. by selecting a drink-code from a menu where the selected drink-code is associated with the "target image") a target image, the user also implicitly selects a 'target drink'—e.g. that it is intended to print abc.jpeg onto a large cappuccino and not onto a beer or a small cappuccino.

N) 'drink property data' describes one or more of (i) contents of a drink and/or (ii) the container in which the drink resides. Examples of drink-contents properties include but are not limited to type of drink (i.e. alcoholic vs. non-alcoholic, coffee vs beer vs wine (e.g. sparkling wine)), temperature of the drink, properties (e.g. concentration, particle-size distribution) of particles within the drink, property(ies) of froth or foam at an upper surface of the drink (e.g. foam thickness, bubble size, viscosity, color), and drink color. Examples of drink-container property include (i) size of the drink container; (ii) symbols or codes or drawings or text on the drink container (e.g. drink sidewall); (iii) color of the drink container. For any embodiment referring to a 'drink property,' (i.e. generically), the drink property may in any embodiment refer to any specific drink property described herein.

In one specific example, the 'analysis circuitry' may, for example, compute a 'size' of the drink by edge detection—e.g. by a camera viewing the rim of the beverage container from above.

I) "Current drink property data' versus 'target drink property data'—

I1) One example of 'drink property data' is 'current-drink property data' relating to a drink currently supported by a platform (e.g. elevatable tray) of the drink printing machine—current-drink property data may be sensed by a sensor (e.g. camera, weighing scale, chemical sensor, optical device other than a camera, thermometer (e.g. infra-red based) etc).

I2) Another example of 'drink property data' is 'target drink-property data.' Thus, if before the printing (e.g. and before the 'user' selection of a drink-code)) a drink-code and/or a drink-image may be associated (e.g. within the 'menu' presented on the screen) with a specific 'target drink.' For example, a customer may request to print a certain 'selfie' or other photograph onto a cappuccino drink. As discussed below, this request may come in stages—in one example, first the customer uploads the image or a specification thereof and only later does the customer specify the 'cappuccino.' In this example, a retail establishment (e.g. restaurant) may process different types of drinks on a single drink printer—i.e. the drink printer may be used both to print on coffee or on beer, or on different 'types' of drink beverages.

Thus, in this example, once a 'large cappuccino' is specified as a 'target drink,' the known properties (i.e. exactly or approximately) may be available in memory or storage—e.g. the size of the 'target drink,' chemical properties of the target drink (e.g. beer vs. coffee, etc), symbols or codes that are excepted to appear on a surface of container of the target drink (e.g. it is expected to write the word 'cappuccino' on the sidewall of the cup), etc—all of these are examples of 'target drink properties' "Target drink properties' may be properties of the content of the 'target drink' of the container.

As discussed below with reference to FIG. 13A, the target drink properties may be compared to 'current drink' properties before printing to make sure that the intended (or 'target') pattern is printed on the correct drink (i.e. and not 'accidentally printed on the 'wrong drink').

H) a 'drink-match parameter' describes whether or not two drinks are the same and/or the likelihood that they are the same. It can also describe a similarity between two drinks. In one example, the 'drink-match parameter' has a value 0 and 1 where '0' is a 'bad match' and 1 is a 'perfect match.' In this example, a 'drink-match parameter' between a 'small capuccino' and a large beer is 0.001; a 'drink-match parameter' between a 'small capuccino' and a large capuccino' is 0.6 and a 'drink-match parameter' between a 'small capuccino' and a medium capuccino' is 0.8.

I) "Imaging a drink'" (e.g. current drink) may refer ti any of the following: imaging the entire drink, imaging a portion of the drink, imaging the drink's container, imaging a portion of the drink's container The closer the value to 1 the more likely there is a match.

Figure 1B:
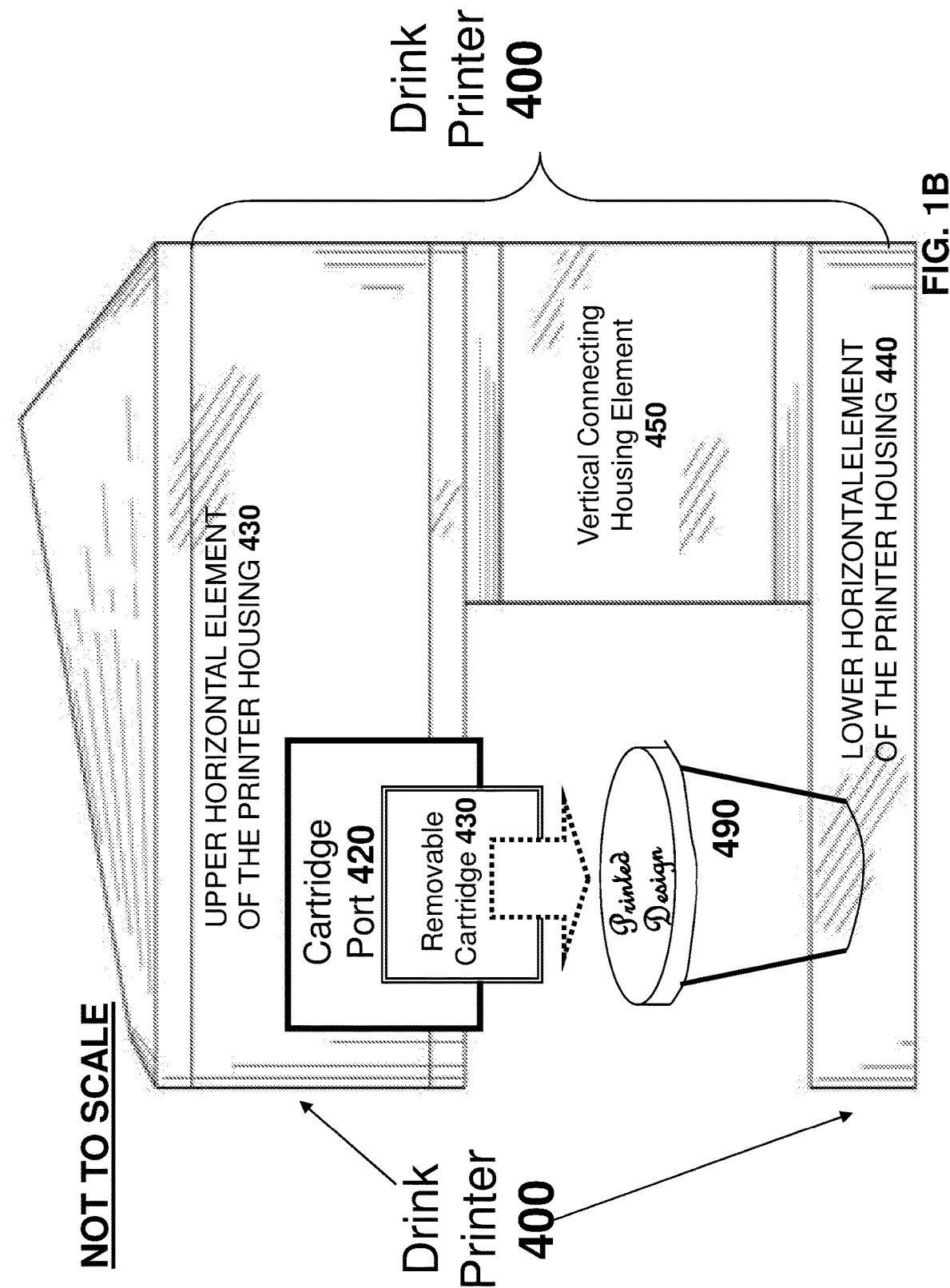
Figure 2:
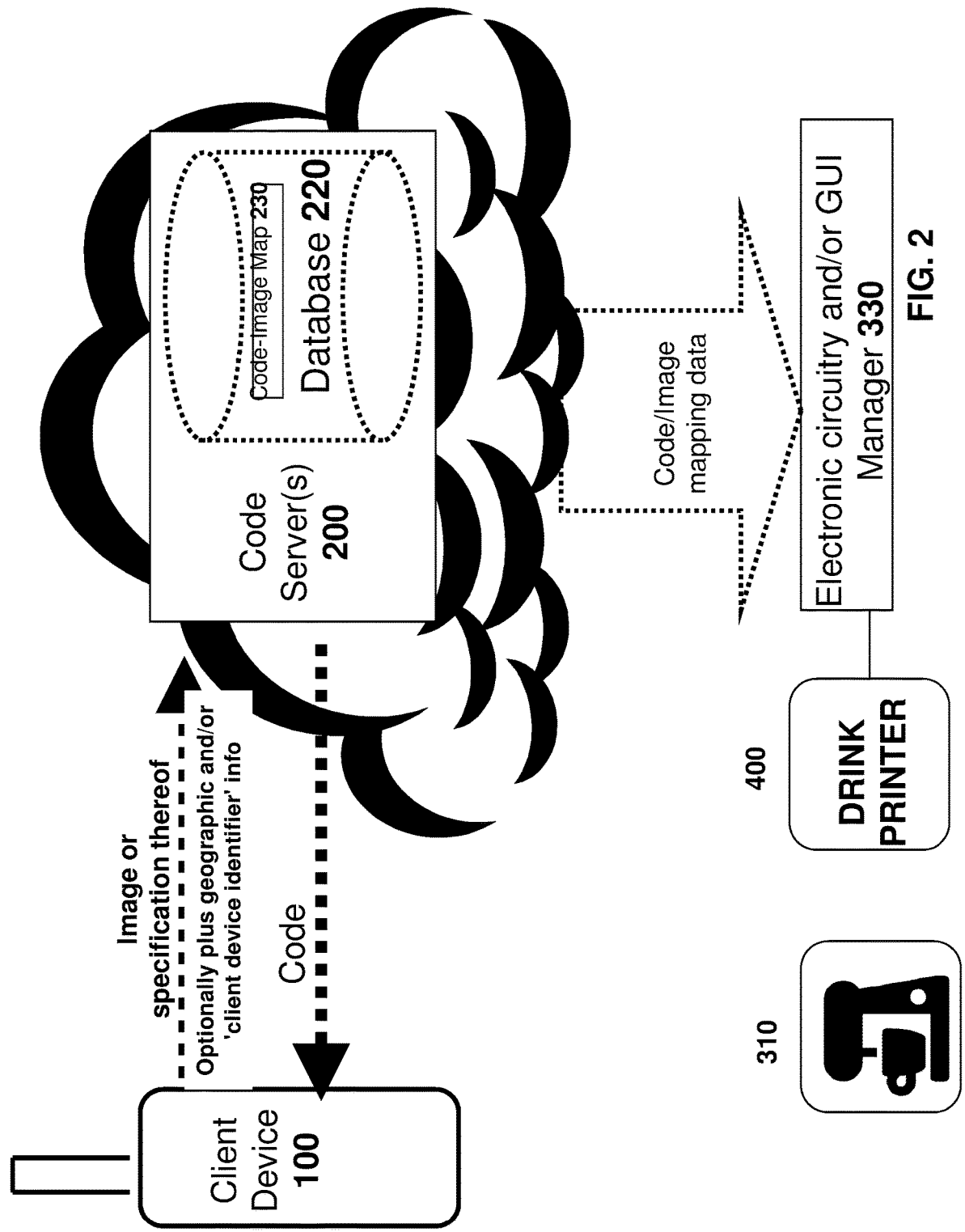

FIGS. 1A-1B illustrate a drink-printer device 400 operative to print designs (i.e. by droplet-deposition) on a surface of a beverage within beverage container 490 (e.g a cup). The printer device comprises a housing, a cartridge portion 420 within the housing, and a tray 470 (e.g. vertically elevatable to move up and down). As shown in FIGS. 1A-1B, the housing drink printer 400 includes an upper horizontal portion 430 above the beverage container 490 (i.e. when on tray 470), a lower horizontal portion 440 below container 490 and/supporting container 490, and a vertical connecting housing element 450 (e.g. supporting upper horizontal portion 430). For example, when the printer begins the print first container 490 is lifted up towards nozzle(s) of cartridge 430 by vertical motion of tray 470—e.g. the container 490 may be lifted by at least 5 cm or at least 10 cm The drink-printer device 400 (e.g. thermal ink-jet device) comprises a cartridge port 420. Removable cartridge (e.g. comprising a reservoir of edible ink—e.g. coffee based) is deployed to cartridge port 420. In some embodiments, drink printer 400 is a thermal inkjet printer. The downward block arrow in FIG. 1B represents ink droplet deposition to form a pattern on an upper surface of the beverage within container 490. The term 'drink printer' is a device to form a pattern on a surface of a beverage by droplet deposition. Typically, drink printers are configured so that the pattern is formed by lateral and longitudinal movement of ink-deposition nozzles (e.g. of cartridge 430). In some embodiments, the pattern applied to the upper surface of the beverage is formed solely by lateral and longitudinal motion of the nozzles while beverage (and container 490) are held stationary. The skilled artisan is referred to PCT/IL06/00851 filed 23 Jul. 2006 which published as WO2007013061, incorporated by reference in it's entirety. Different embodiments relate to any feature (or combination of features) combined with any feature (or combination features) disclosed in the present document.

Device 400 also includes display screen 260 (e.g. 'touchscreen')—e.g. deployed to and/or embedded within a housing of the drink printer 400 (e.g. upper portion 430 of the housing—e.g. an upper surface of upper portion 430). In some embodiments, screen 230 is slanted. The screen 260 has a user interface.

For example, a plurality of codes (e.g. textual codes) are displayed (e.g. simultaneously displayed) where each code is associated with a different image to print onto the beverage. Thus, in one example (see FIG. 1A), when the user engages code AD34 a first image (e.g. first .gif) is printed—e.g. a picture of an animal, when the user engages a second code 9ZA2 a second image (e.g. a second .gif) is printed (e.g. the script/cursive words "Printed Design") is printed, and so on.

Towards this end, some sort of mapping is electronically stored (e.g. in a location that is 'local' to printer 320 or in any other location). This map is between digital graphical images and codes (e.g. textual codes). The term 'graphical image' is used broadly to refer to images generated by computer graphics, photographs, text, or other content—a 'graphical image' may be provided as a .gif file, a .jpeg file, a .tiff file, a .pdf file, or any other data-object known in the art.

Figure 3:
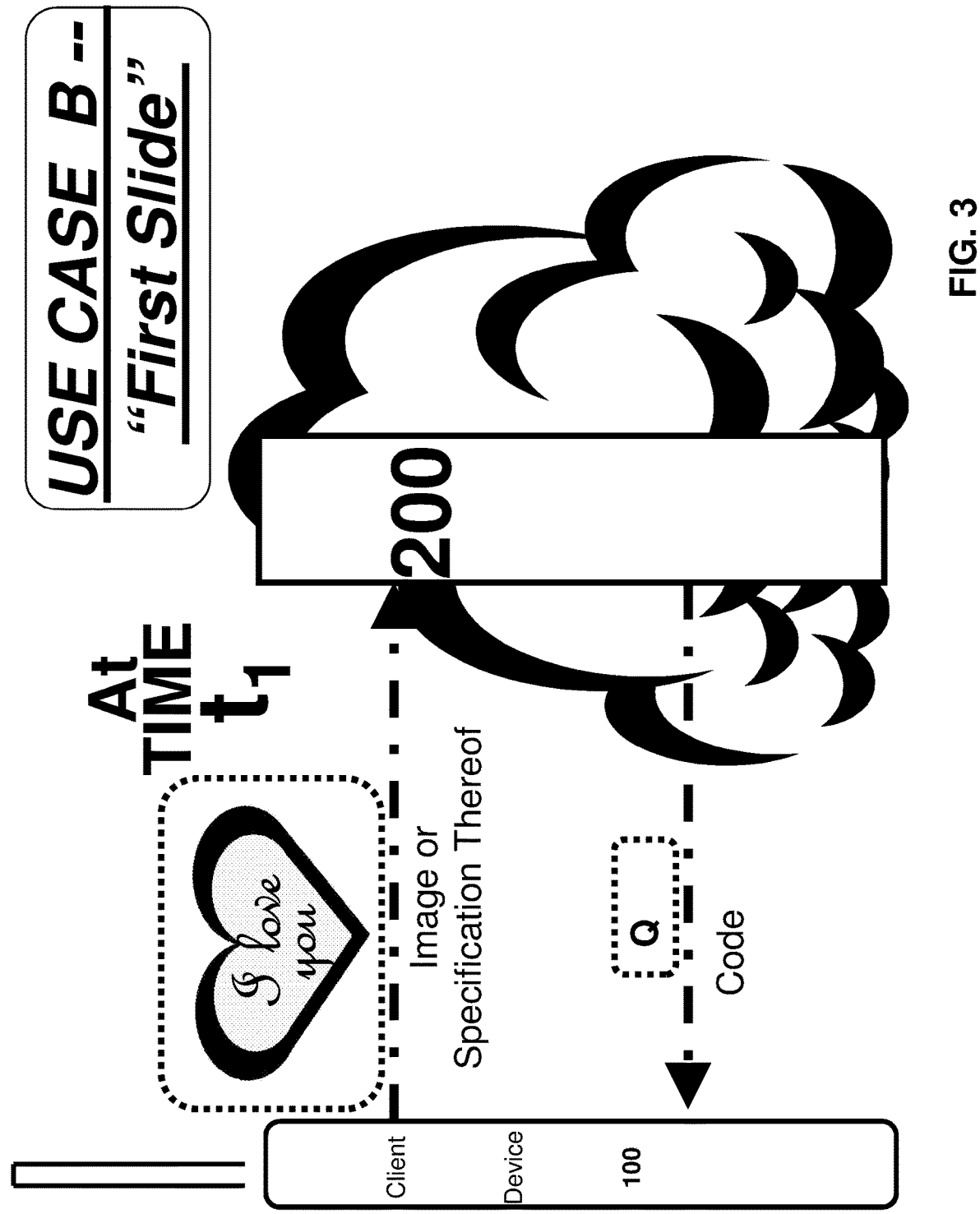

FIG. 3 illustrates a system where user(s) specify a desired image to print on a beverage using a client device 100. In one example, a menu of images may be displayed on a screen of client device. In another example, client device may include some sort of image-generating software for generating an image on the client device. In another example, client device may include an onboard camera (not shown) for acquiring an image of a scene. The image (or a specification thereof—e.g. the user selects an image from a plurality of digital graphical images located in the cloud) is uploaded to code server(s) 200 which assigns and/or maps a code (e.g. textual code) to the image to 'specify an association' (or mapping) between the textual code (e.g. generated by code server) and the user-provided (or specified) image provided and/or specified by client device 100. Optionally, code server 200 sends the code back to client device 100.

Code Server 200(s) may send code/image mapping (or 'association') data to drink printer 320 to electronic circuitry. For example, if a new code is generated by code server(s) and associated with the digital graphical image, code server(s) 200 may send a specification of a mapping between the digital graphical image (e.g. there may be a pre-determined bank of N images stored locally at drink printer 320 and the 'specification' may relate to 'Image number 262') and the textual code. In some embodiments, the actual image (e.g. a digital image) is sent from client device 100 to electronic circuitry and/or GUI manager 300 9e.g. by or via code server 200).

"Electronic circuitry" may include any software/executable code module (i.e. stored on a computer-readable medium) and/or firmware and/or hardware element(s) including but not limited to field programmable logic array (FPLA) element(s), hard-wired logic element(s), field programmable gate array (FPGA) element(s), and application-specific integrated circuit (ASIC) element(s). Any instruction set architecture may be used including but not limited to reduced instruction set computer (RISC) architecture and/or complex instruction set computer (CISC) architecture.

Thus, client device 100 specify digital images (e.g. according to user input) and subsequently (e.g. in response) a code 'matching' the digital image appears on display screen 260. The mapping between the image and the code (e.g. textual code) may be generated by coder server(s) 200.

Use Case A

In one use case, a user ("Robert") is in a coffee shop with his/her spouse and wants to print a photograph of the user together with his/her spouse on their drinks. The user operates client device 100 to specify the image to upload the photograph to code server(s) 200 which assigned a code (e.g. textual code) to the photograph image and sends the photograph along with the 'association data' to GUI manager 330. At that time, the text ("XYZ" for this example) appears (e.g. in response to the uploading of the photograph by client device 100) on the screen 260 of drink printer device 400.

At a later time, the user verbally places his/her order at the cashier within the coffee shop—he orally tells the cashier that s/he wants a large cappuccino and shows the display screen of his/her client device 100 which displays the code mapped to the image (e.g. the photograph of the two spouses) that was received by code server(s) 200.

The cashier then takes a disposable cup and on the outside of the cup writes "Robert" and "Large Cappuccino" and "XYZ") on the outside of the cup which is handed to the barista. The barista operates both drink manufacturing machine 310 (e.g. a coffee machine) which dispenses the contents of the drink into the container 290 and drink printer 400. First the barista reads the words Large Cappuccino on the cup and produces (using machine 310) a large cappuccino. Then the barista reads the text code "XYZ" and selects (e.g. from the menu of display screen 260) the "XYZ" option. When the user selects XYZ using the GUI of printer 400 the machine then prints the photograph of Robert and his/her spouse.

Another customer in the coffee shop named "Steve" may, at the same time that Robert uploads the photograph of him with his spouse, specify a 'Lion King' image from a bank of images stored in the crowd. Steve would receive a different code (e.g. "ABC") which would be mapped to the "Lion King" image (and not to the picture of Robert with his spouse). In response to Steve specifying the lion code image (i.e. uploading a specification of this image), the code "ABC" appears on the menu of display screen 260. Steve wishes to order a hot chocolate beverage. Steve simply tells the cashier that he desires a hot chocolate and specifies "ABC"—the cashier than writes on the cup "Steve" and "Hot Chocolate" and "ABC") on the outside of the cup which is handed to the barista. Because there is mapping/association data between the "ABC" and the lion king, when the barista engages the "ABC" on the screen 260, the Lion King Image will print. Thus, in this example, when the barista receives the cup it will be clear that s/he needs to generate a hot chocolate using production machine 310 and then select the 'ABC' code to print the image on printer 340.

From this simple use case we see that in a retail environment (e.g. from many customer, each specifying his/her own customized drink) where there are multiple types of drinks generated by production machine 310, use of the text code helps the staff print the 'correct image' on the 'correct drink.'

In the above example, there was no need for client device 100 to specify the contents of the drink—only the image. In other examples, client device 100 may specify the contents of the drink (i.e. the s/he wants a cappuccino or a hot chocolate)—for example, if production machine 310 and printer 340 are integrated into a single machine, the cashier would just write "Robert XYZ" on the cup and the barista would just select the "XYZ" option. In this example, the code "XYZ" would map both to the contents of the drink and to the image (e.g. Lion King image).

Use Case B (FIGS. 3-6)

Figure 4:
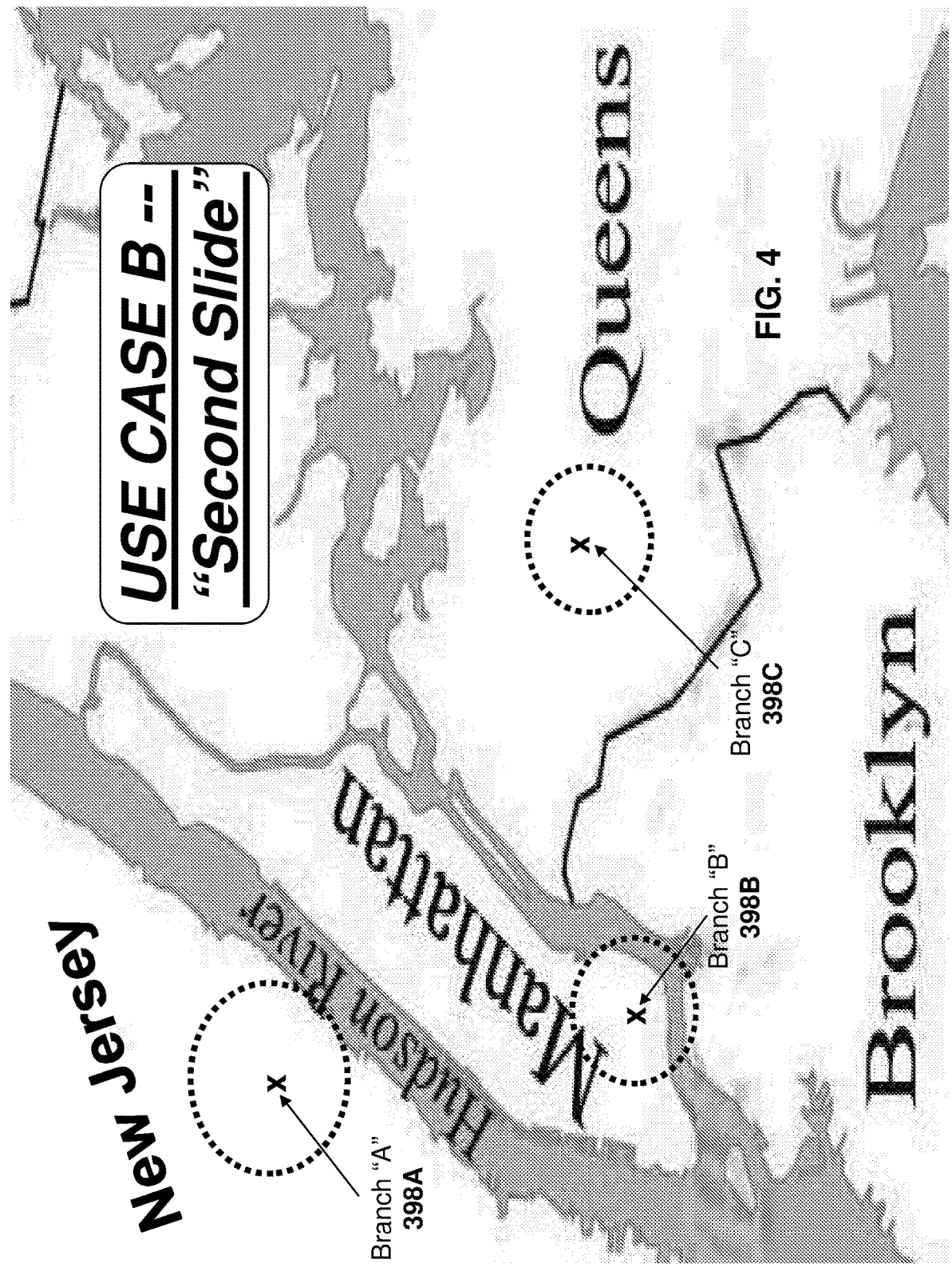

This case relates to a chain of coffee shops having branches in various geographic locations. As shown in FIG. 4 this may include branch A 398A in New Jersey, branch B 398B in downtown (i.e. North) Manhattan and branch C 398C in Queens.

Each branch has its own set of one or more drink printer(s) therein. In FIG. 3, the user uploads and/or specifies an image to print (e.g. "I love you" in a heart) and mapping server 200 assigns code "Q" to the image specified via Client Device 100. Optionally, the code 'Q' is sent to client device 100.

Figure 5A:
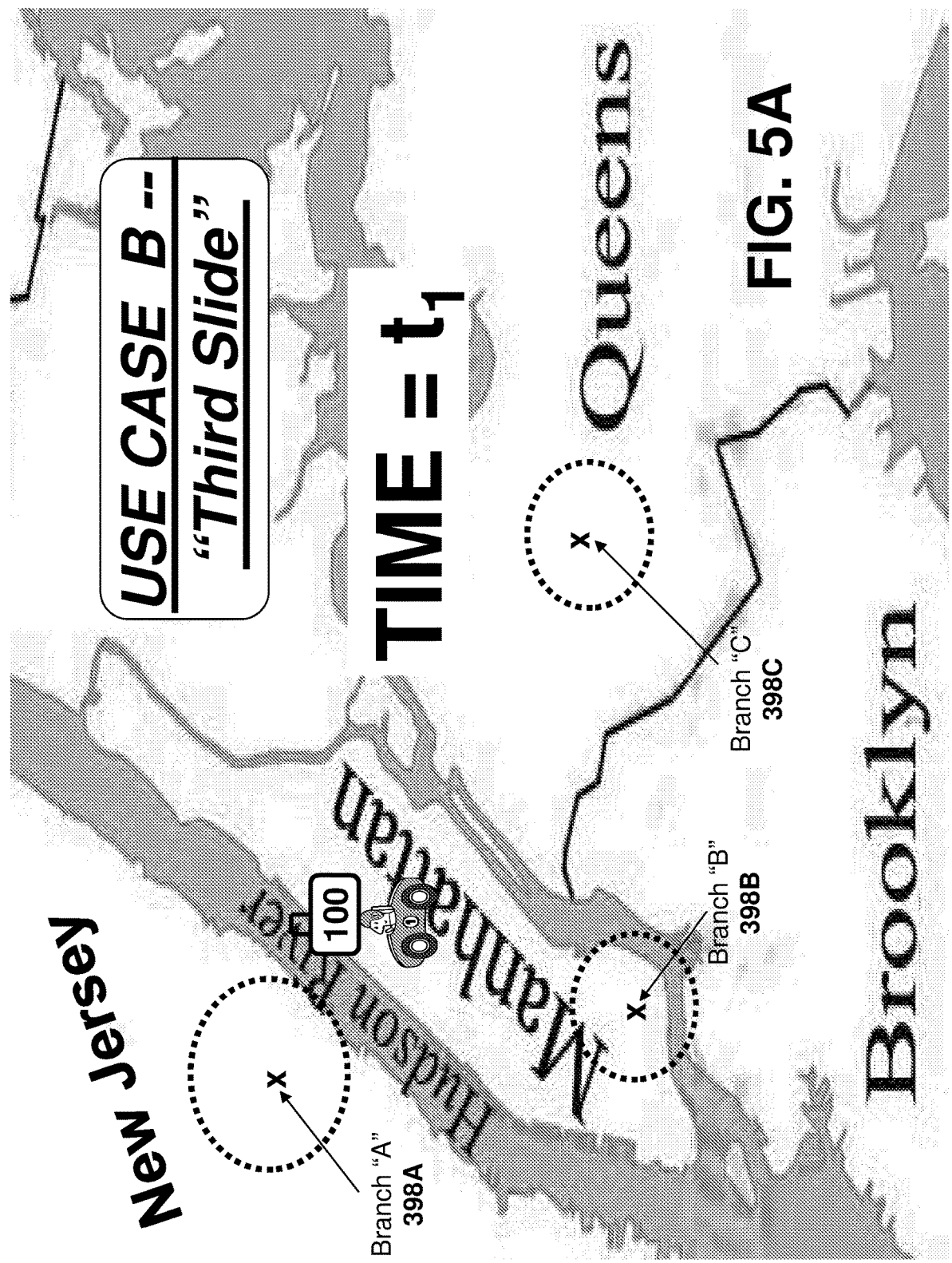

As shown in FIG. 5A, the user is in uptown Manhattan at the time the image is uploaded and/or specified at time t1.

At a later time t2 (FIG. 5B) the user drives to the New Jersey branch—in response to the user going into geographic proximity with the Branch A 398A, code "Q" appears on GUI of printer 400A in Branch A 398A (e.g. on screen 260 of printer 400A) and the 'mapping data' between the image (e.g. "I love you" in the heart) provided by device 100 at time t1 is available at time t2 to printer 400A in branch 398A. Thus, at time t2 if an operator selects code "Q" in branch A 398A the image "I love you in a heart" is printed onto the drink—however, at time t2 the code "Q" either does not appear on the display screen of printers 400B-400C in branches 398B-398C or is mapped to a different image.

Figure 5C:
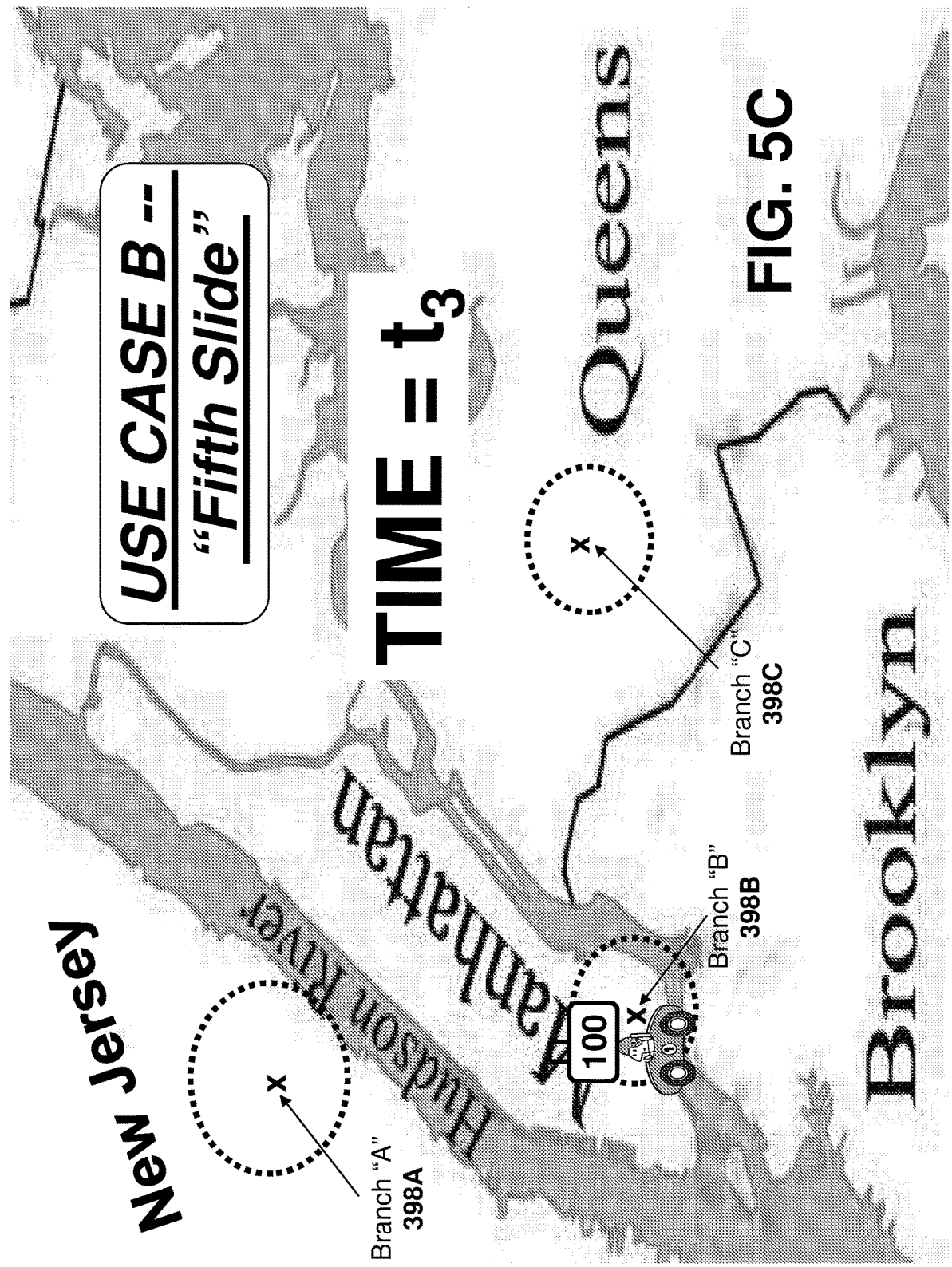

As shown in FIG. 5C, at a later time t3 the user may not purchase the drink in 'branch A" and may instead travel to 'branch B"—at this time t3, the code 'Q' is either not available on the menu/GUI in 'branch A' 398A or mapped to a different image. At this time t3, if an operator selects code "Q" in branch B 398B the image "I love you in a heart" is printed onto the drink.\

Figure 6A:
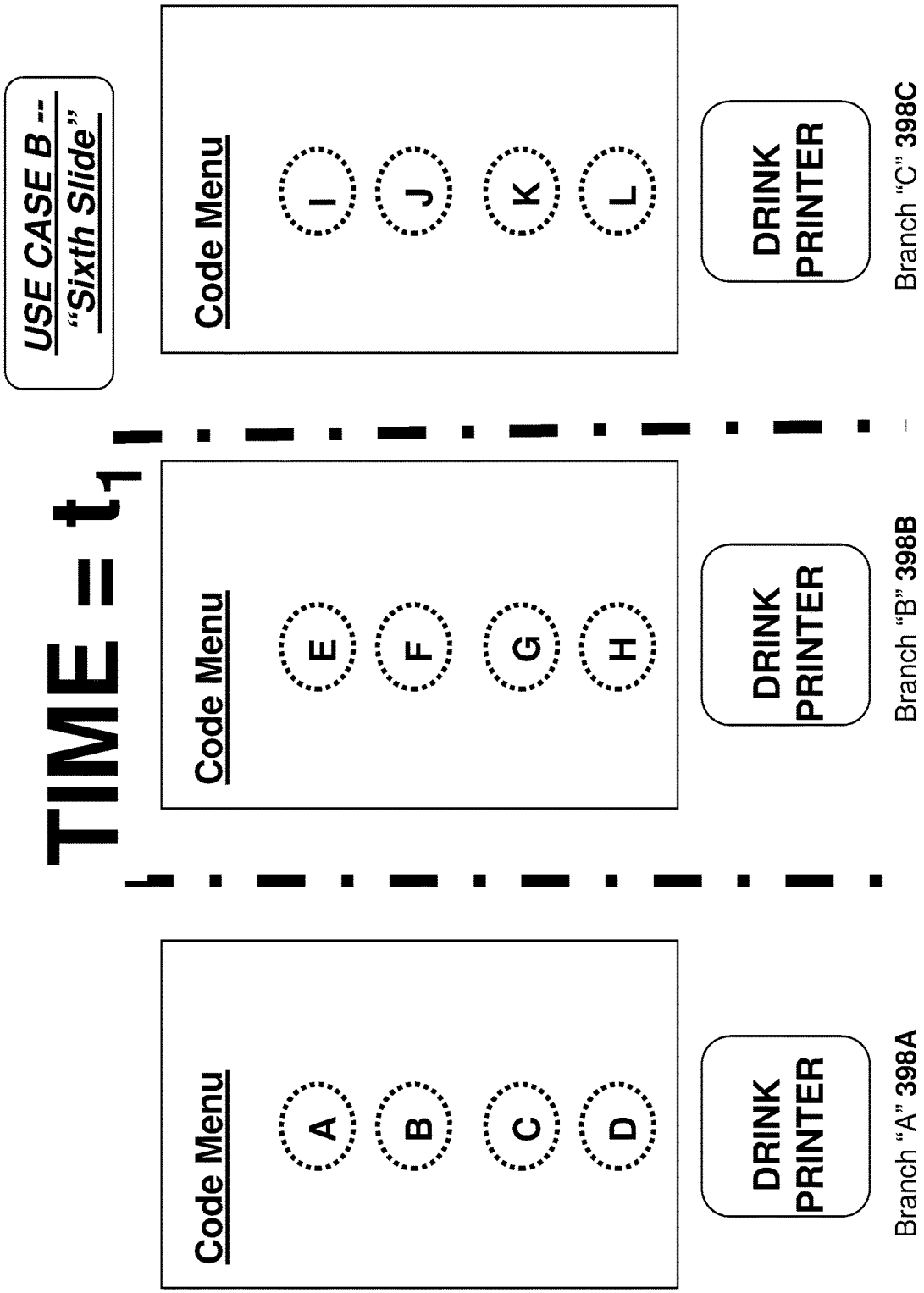
Figure 6B:
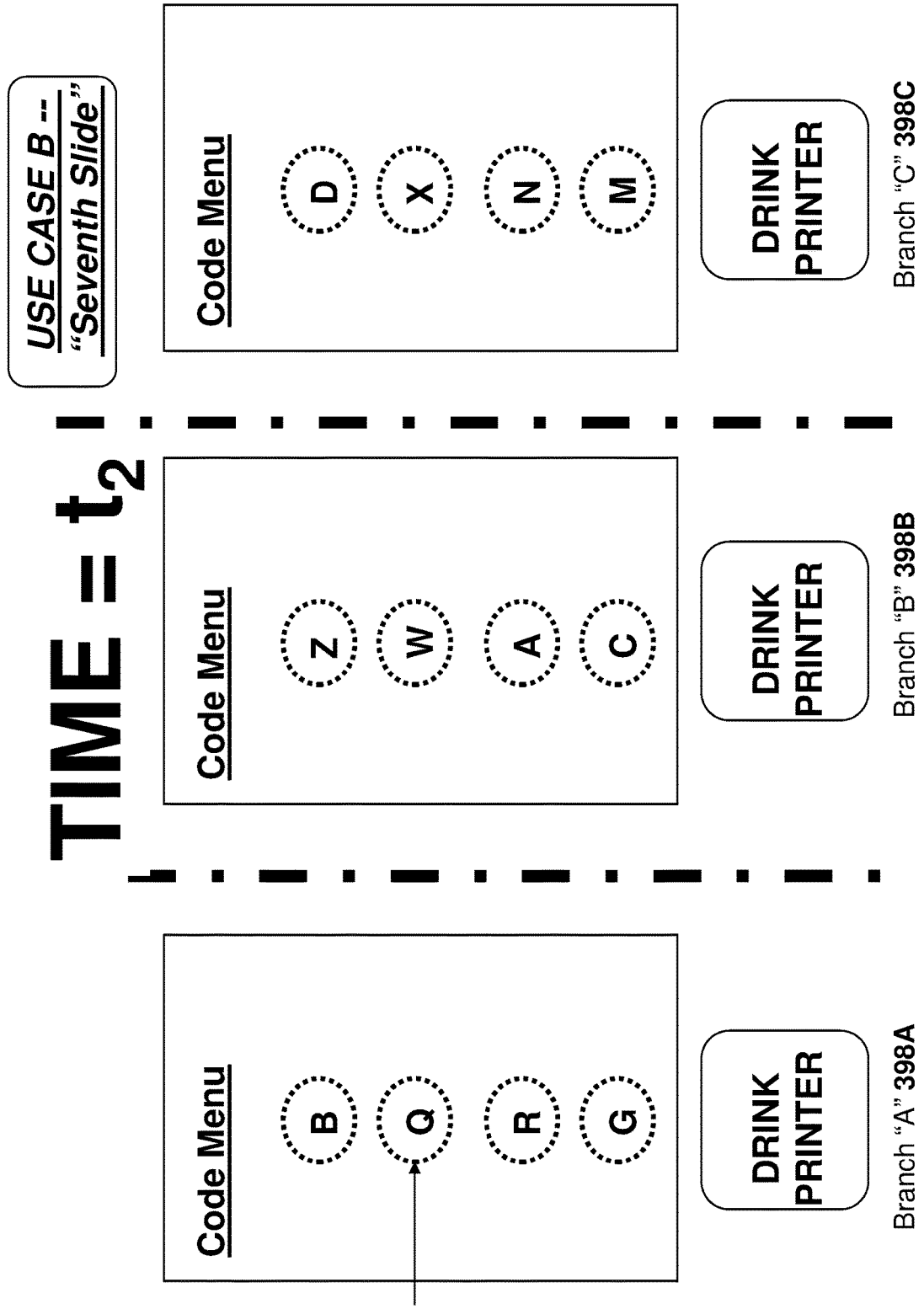

FIGS. 6A-6C illustrate the GUI/menus (e.g. on screens 260 of drink printers 400A, 400B and 400C respectively) at times t1-t3. Thus, initially, the 'Q' code does not appear on any menu. In FIG. 6B, in response to the user travelling to the vicinity of branch A 398A, the "Q' code of the user appears on the menu in "Branch A" 398A only (and is mapped to the 'I love you image" only for the printers in branch A 400A).

In FIG. 6C, in response to the user travelling to the vicinity of branch B 398B, the "Q' code of the user appears on the menu in "Branch B" 398B only (and is mapped to the 'I love you image" only for the printers in branch B 400B).

In one implementation, when the user uploads and/or specifies the image in FIG. 3, an identifier of the user's specific client device 100 or of a "SIM" thereof is also mapped to the image and the text code. For example, in FIG. 3 the client device may have device ID "IDXYZ." The location of the device 100 (or SIM) can be tracked and when it is reported to 'code server' that device 100 having device ID "IDXYZ" is in the 'vicinity of branch A,' the code 'Q' (i.e. which is associated with both "IDXYZ" and the "I love you image") is available on the GUI of printer 400A in branch A 398A and associated with the "I love you image."

Use Case C (FIGS. 7A-7D)

Figure 7A:
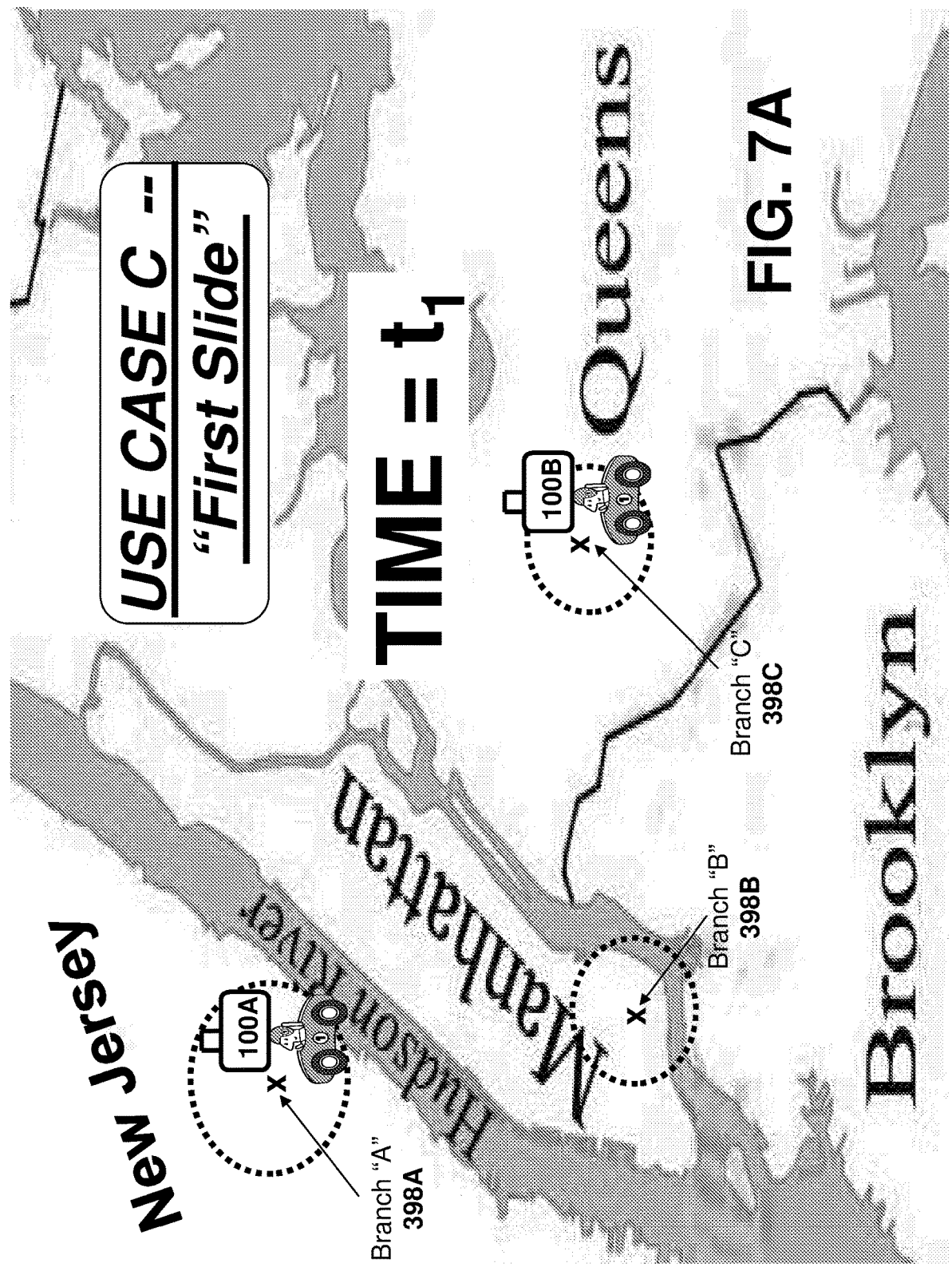
Figure 7B:
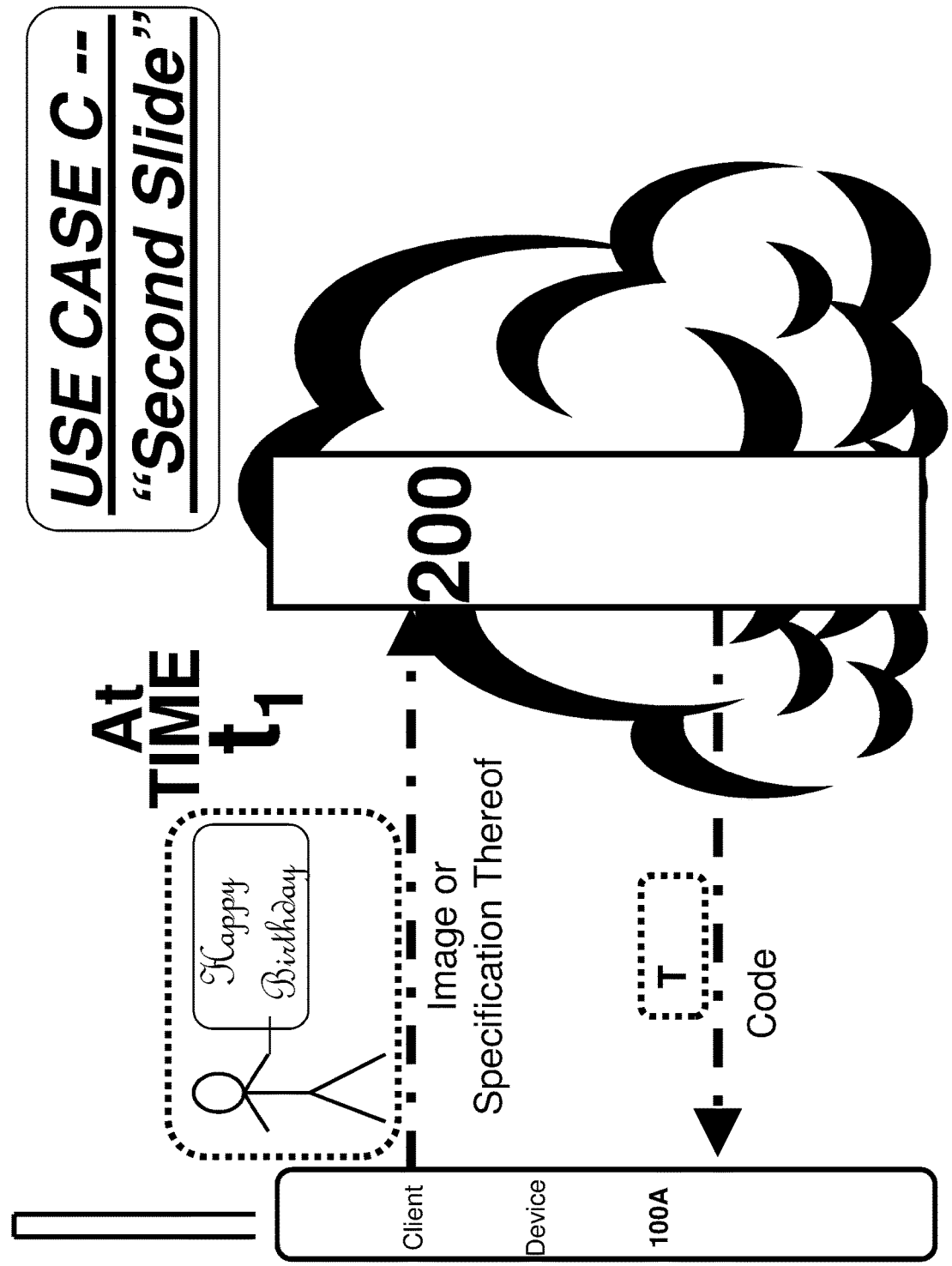
Figure 7C:
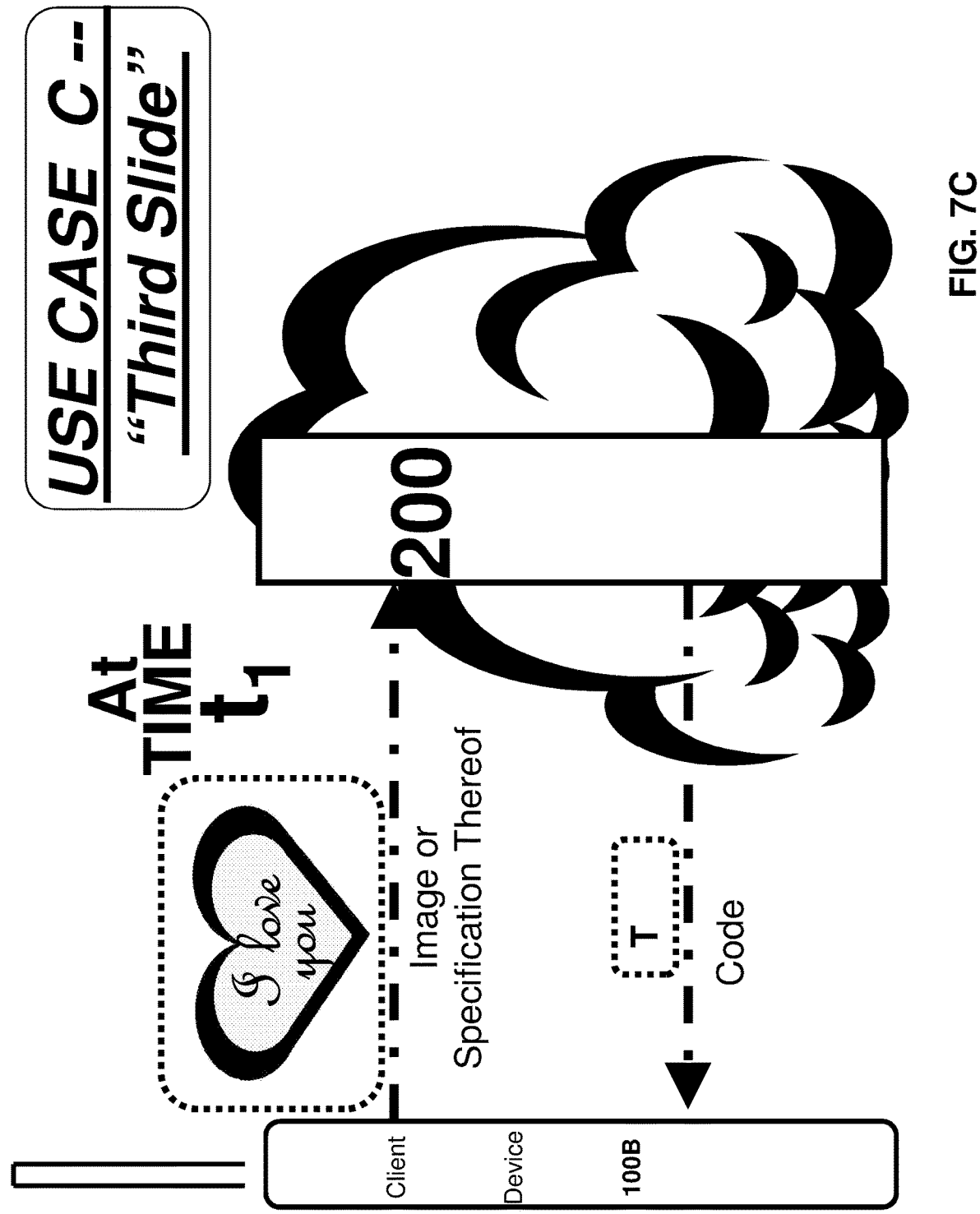
Figure 7D:
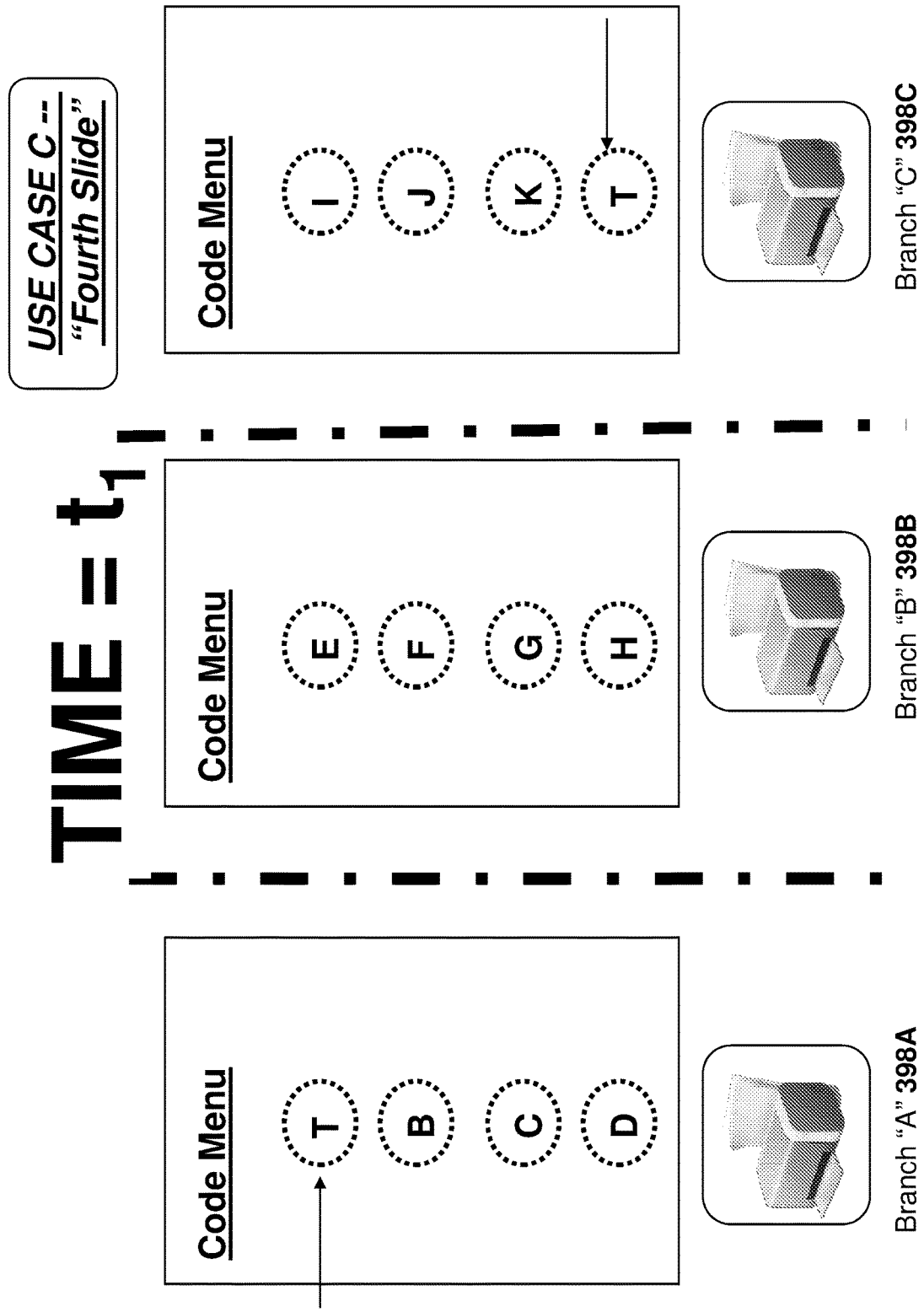

In this use case, there are two users—a first user having terminal 100A in branch A 398A at time t1, and a second user having terminal 100B in branch C 398C at time t1. As shown in FIGS. 7B-7C, the first user wishes to print a 'happy birthday' image and is provided with code "T"—the second user wishes to print an 'I love you' image and is provided with code "T"—these are 'clashing codes.' Allowing for 'Clashing codes' between different geographic locations/branches may be advantageous because this allows for shorter codes. As shown in FIG. 7D, the clashing codes are handled according to geographical locations—in Branch A 398A engagement of the "T" code will provided the happy birthday' image because the client device 100A is in branch A 398A, and in Branch C 398C engagement of the "clashing" "T" code will provided the "I love you" image because the client device 100C is in branch A 398C—these images are specified and/or generated and/or uploaded by different client devices and this information is tracked and used to populate and/or specify the image printed by a code of the GUI.

Thus, the 'activity' of the code 'follows' the client device 100 which generates and/or specifies and/or uploads the image.

FIGS. 8A-8B

FIGS. 8A-8B are flow-charts of methods of operating drink printers and client devices. Thus, in FIG. 8A, only if the client device 100 is 'local' (e.g. according to geographic proximity—this can be pre-defined) to a drink machine does the code specified by client device 100 appear in the GUI of printer 400 (or appear as 'mapped' to the image specified by client device 100). Steps illustrated in FIG. 8A are S61, S65, S69 and S73. In FIG. 8B, as the client device which specified the image moves into the vicinity of a printer 400, its code becomes available and/or active on a display screen 260 thereof.

Steps illustrated in FIG. 8B are S81, S85, and S89.

Figure 9A:
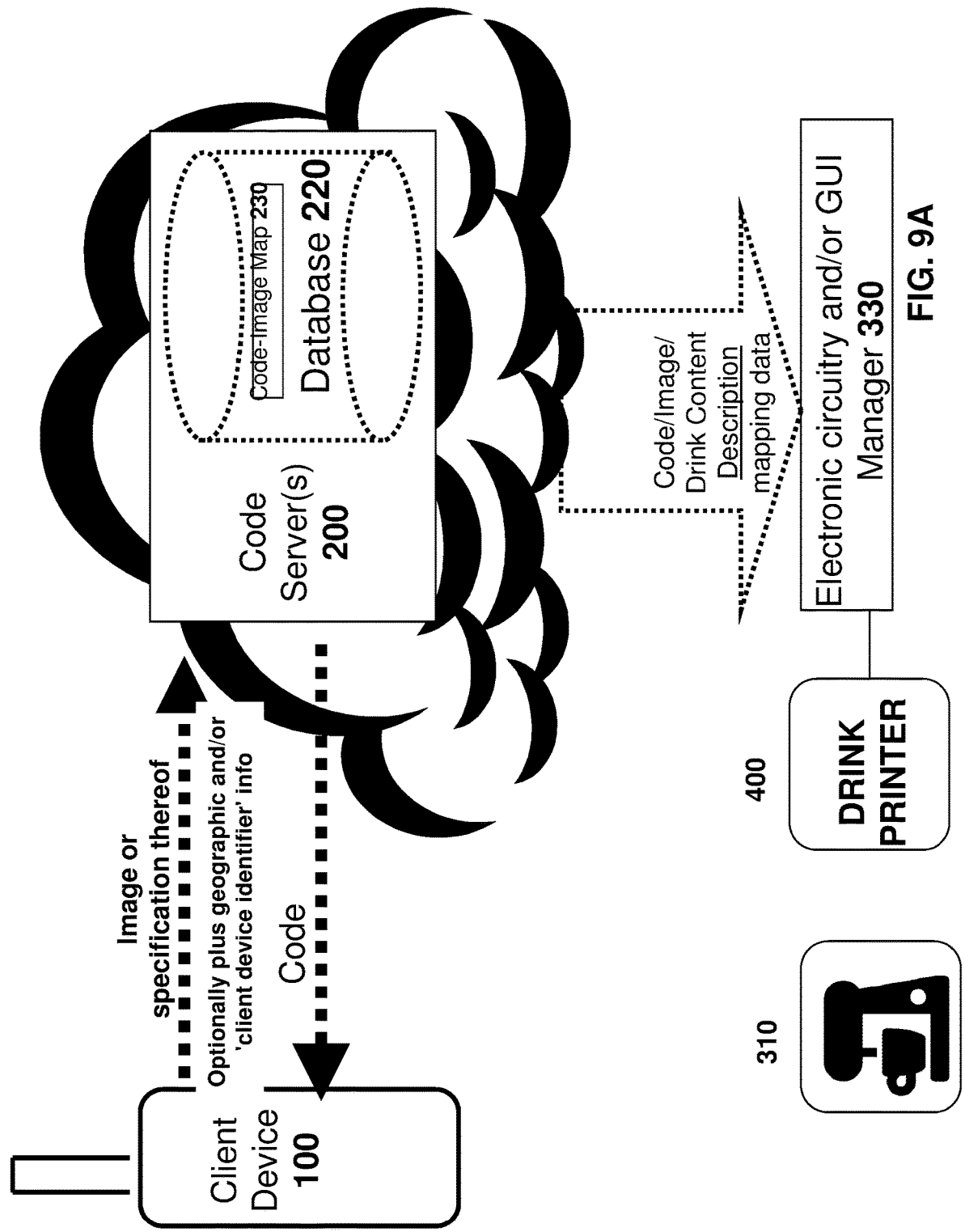
Figure 9B:
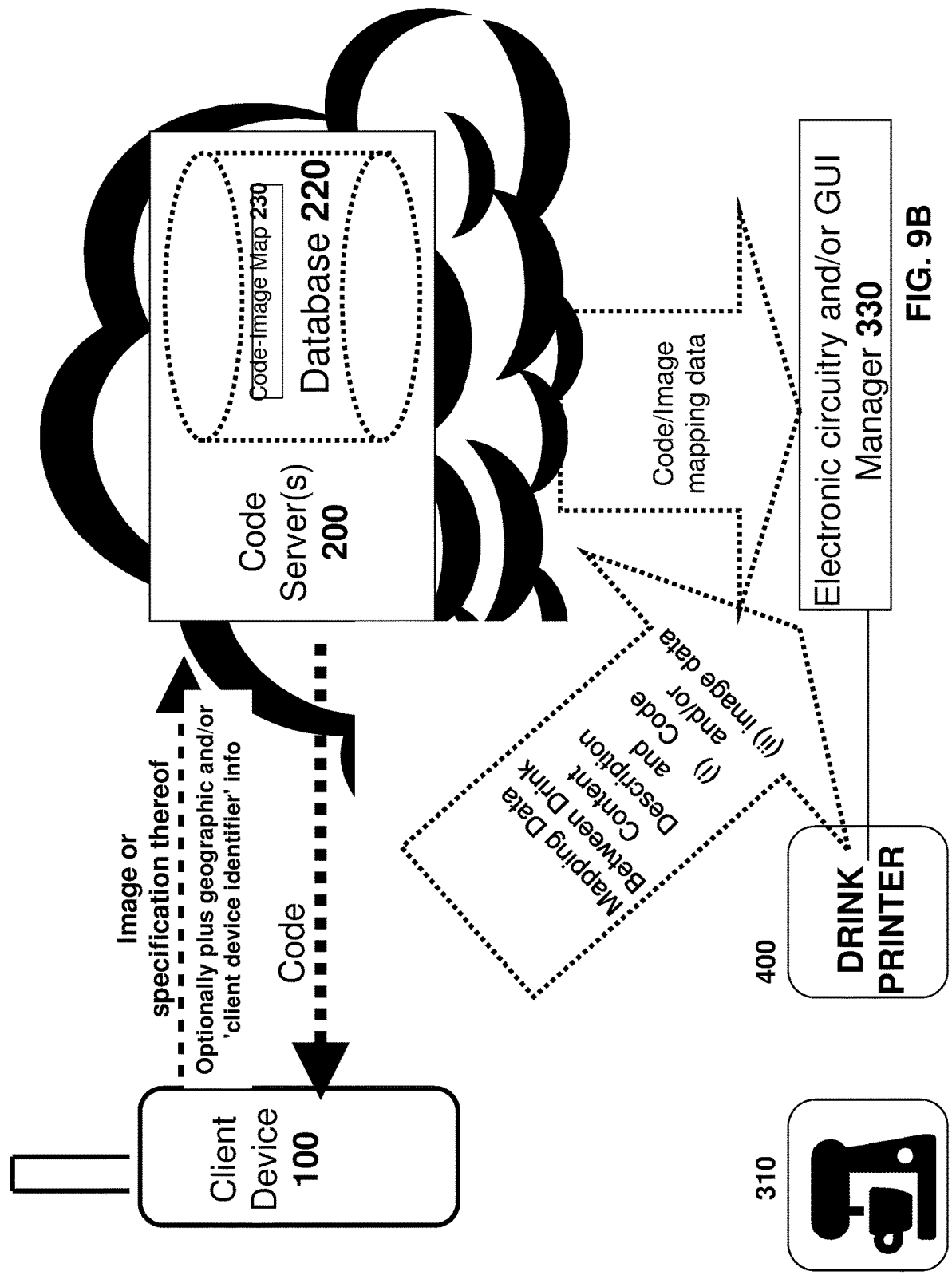
Figure 10:
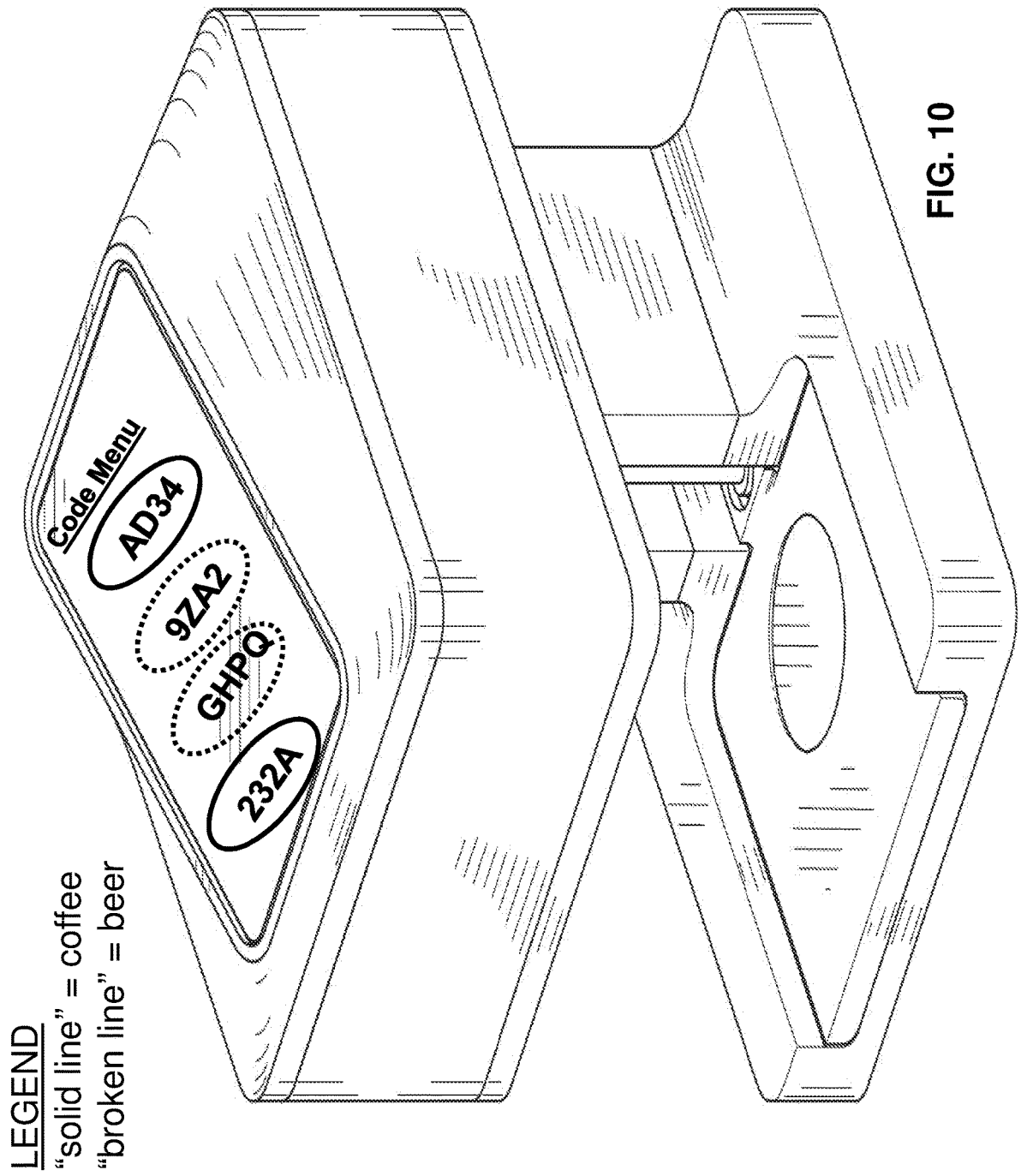

A Discussion of FIGS. 9-11

In the example of FIGS. 9-11, the client device may also specify information about the content of the drink itself. In one example, client device 100 would specify 'Lion King Image" on "hot chocolate drink. Thus, comparing FIG. 9A to FIG. 2, in FIG. 9A the code is associated with both a digital image to be printed and a description of the content of the drink. In the example of FIG. 9B, the content of the image is specified by client device 100 (as in FIG. 2) but additional data about the 'content of the drink' is required to be provided not together with the 'image data' but in any manner.

Thus, mapping and/or association data between (i) a code (e.g. text code) (ii) content of the drink and (iii) the image to be printed is available to a GUI manager. In the example of FIG. 10, the same drink printer is used to print both on coffee and on beer—it is desired to avoid situations where the barista would print on the 'wrong drink.' Thus, if the user wishes to select code AD34, s/he would place the cup beneath the nozzles of drink printer 400, and by engaging code 'AD34' the image mapped to code 'AD34' would be printed. In a retail/restaurant environment when there is a need for a barista to print on many different types of drinks (i.e. the same printer can be used to print both on coffee and on beer) without 'mixing up' between drinks, the user interface of FIG. 10 provides the following feature—if according to the 'specification of the content of the drink' and the 'digital image' to print (see FIGS. 9A-9B), a given image (i.e. according to he drink order) should be printed on coffee, the text code is circled with a 'solid line code'; if on the other hand according to the 'specification of the content of the drink' and the 'digital image' to print (see FIGS. 9A-9B), a given image (i.e. according to he drink order) should be printed on beer, the text code is circled with a 'broken line code.'

Thus, before selecting a particular code, the barista may check the actual drink beneath the nozzle (i.e. if it is beer or coffee)—if the drink is coffee, the barista will be careful not to select a code circled by a broken line and if the drink is beer, the barista will be careful not to select a code circled by a solid line.

FIG. 11 describes this process and includes steps S201, S205, S209 and S213. Thus, in step S209, the menu on screen 260 of printer 400 includes information describing an association between the code (e.g. text code) and the content of the drink where the image is to be printed (i.e. beer vs. coffee). When a 'drink order' specifies a particular image (e.g. 'I love you") on coffee, the code (e.g. text-code) for the image appears on the menu of screen 260 visually associated with a 'coffee' indicator (i.e. a rough description of the content of the drink—the coffee indicator is circled by solid line). When a 'drink order' specifies a particular image (e.g. 'Happy Birthday") on beer, the code (e.g. text-code) for the image appears on the menu of screen 260 visually associated with a 'beer' indicator (i.e. a rough description of the content of the drink—the beer indicator is circled by broken line).

Thus, the technique of FIGS. 9-11 may reduce the likelihood that even in a retail environment a barista would erroneously print a given image (i.e. by engaging it's text code) on the wrong drink.

A 'drink-property heterogeneous menu' show keys and/or codes for images to print that are intended and/or targeted for different types of drinks. Thus, if a first image is targeted to print on a coffee beverage (e.g. 'targeted' according to step S205) and if a second image is targeted to print on a beer beverage (e.g. 'targeted' according to step S205) a menu from which the user can specify the first image as well as the second image is a 'drink-property heterogeneous menu.' In contrast, if all images are targeted to be printed on an identical type of drink (e.g. all 'large cappuccinos') this is a 'drink-property homogeneous menu.' Thus, the code menu of FIG. 10 is a 'drink-property heterogeneous menu.'

A printing device for printing on a current drink comprising: a. a tray upon which the current drink rests; b. an ink-jet printer to downwardly ink-jet droplets of ink towards the tray to print an image on the drink supported by the tray; c. a display-screen; d. a mapped drink-code database specifying a map for a plurality of drink-printing codes, between: i. each displayed drink-printing code of the plurality of drink-printing codes; and ii. a respective combination of (i) a respective drink-printing-code-specific target-image to be printed by the ink-jet printer; and (ii) respective drink-printing-code-specific target-drink property-data describing a contents of respective target-drink and/or its container; e. a user-interface for: i. displaying a menu comprising the plurality of drink-printing codes drink-property-heterogeneous on the display-screen such that each drink code is displayed in a manner specific to the respective target-drink property-data associated therewith; and i. receiving a user-selection of one of the drink codes to thereby user-specify, according to the mapped drink-code database, a target-image; a device controller for responding to the user drink-code selection, in accordance with content of the mapped drink-code database, output of the sensor(s) and output of the analysis circuitry, by printing the user-interface-specified target-image onto an upper surface of the current drink.

In the example of FIG. 10, each drink code is displayed in a manner specific to the respective target-drink property-data associated therewith—thus, codes AD34 and 232A are displayed within a solid line indicating 'coffee' while codes 9ZA2 and GHPQ are displayed within a broken line/oval indicating 'beer.' In other examples, the codes may be colored differently—e.g. red characters where the target drink is coffee and blue characters where the target drink is beer. In another example, a different font (e.g. Geneva vs. Times-New-Roman) or font-size (e.g. 12 point vs. 16 point) is used for beer-codes and coffee-codes.

A Discussion of FIGS. 12-13

The example of FIGS. 12-13 describe a technique which also is useful for reducing the likelihood that even in a retail environment a barista would erroneously print a given image (i.e. by engaging it's text code) on the wrong drink.

Figure 13A:
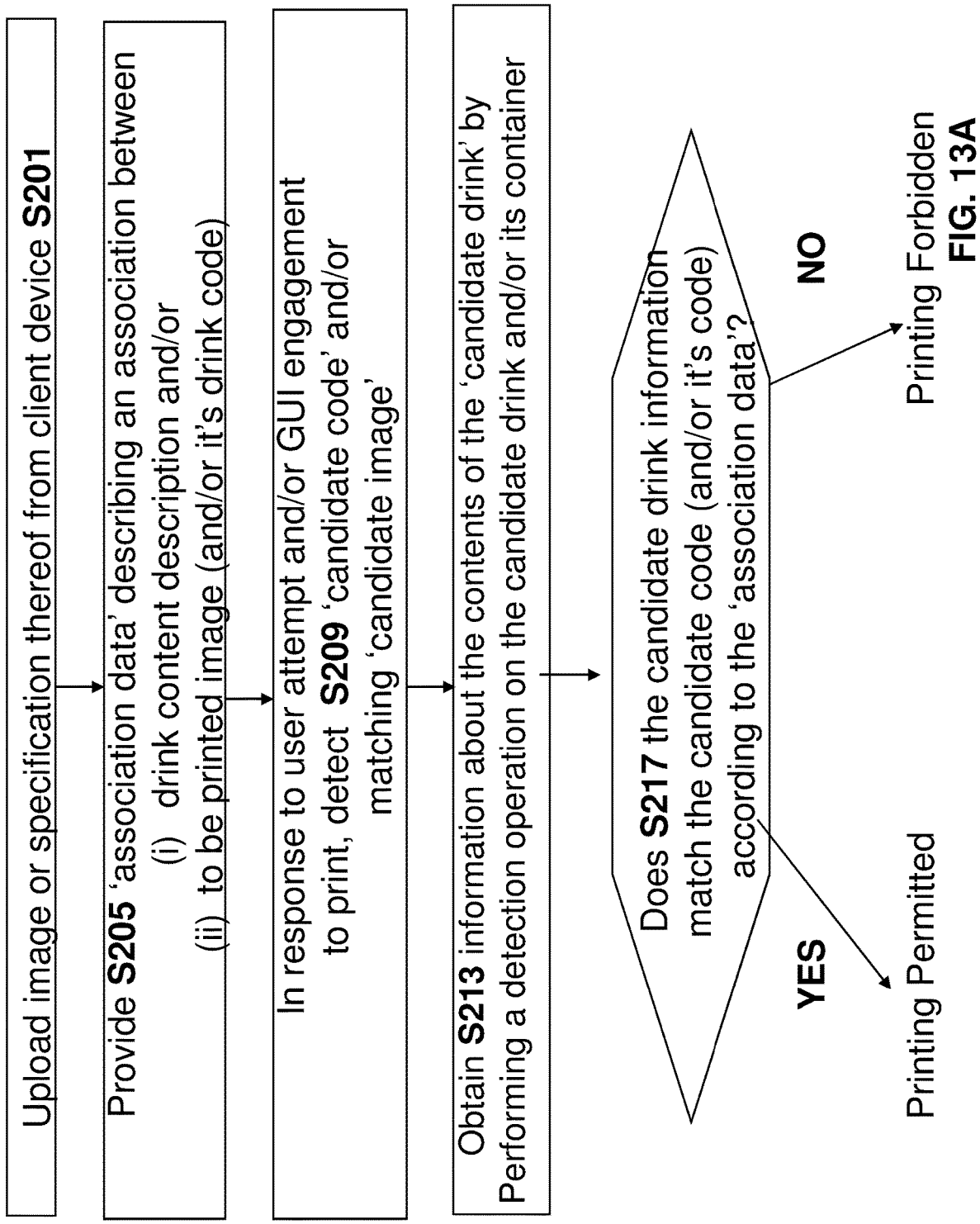
Figure 13B:
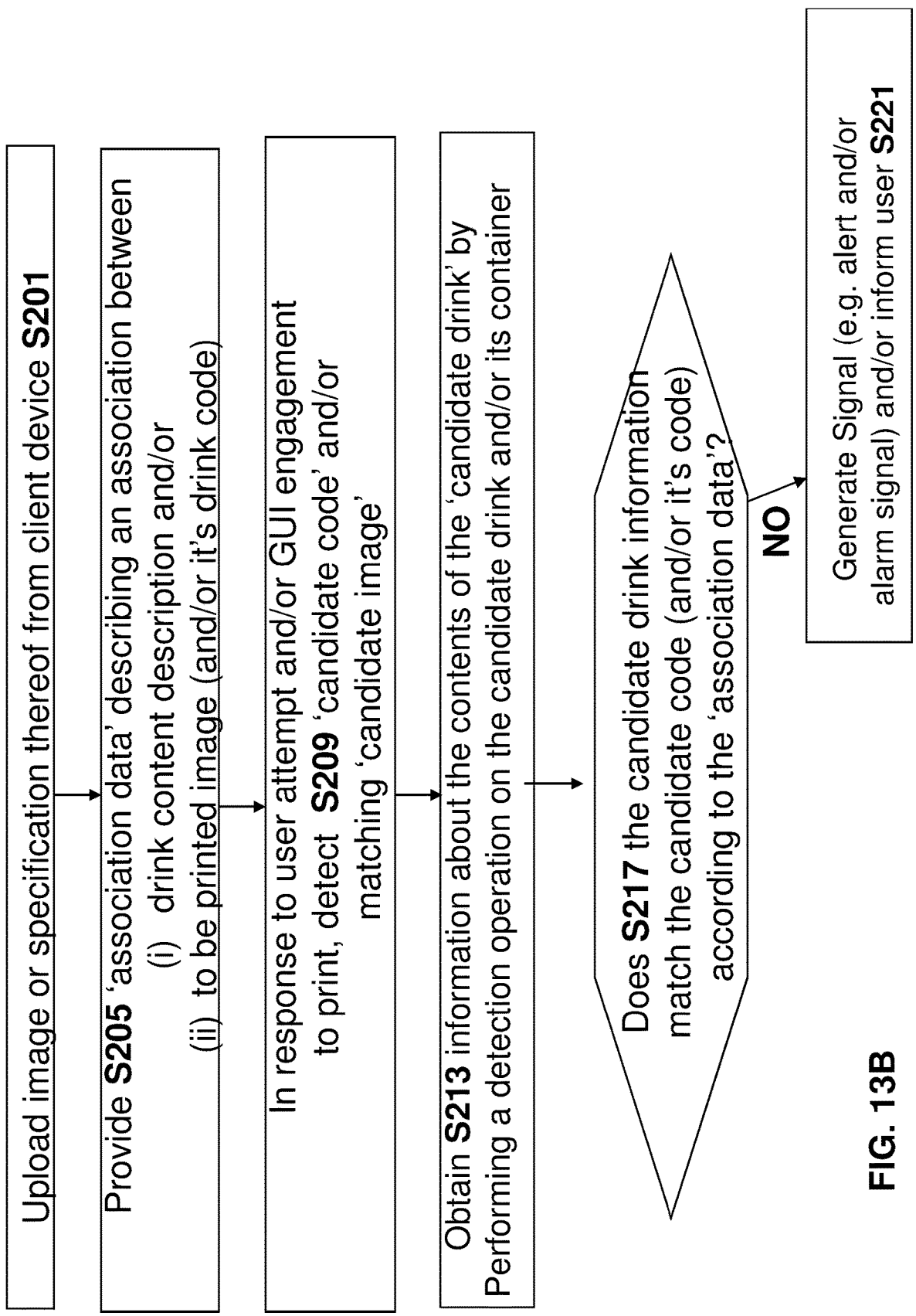

FIGS. 13A-13B include steps S301, S305, S309, S313, and S317. Step 13B also includes steps S321.

Figure 12A:
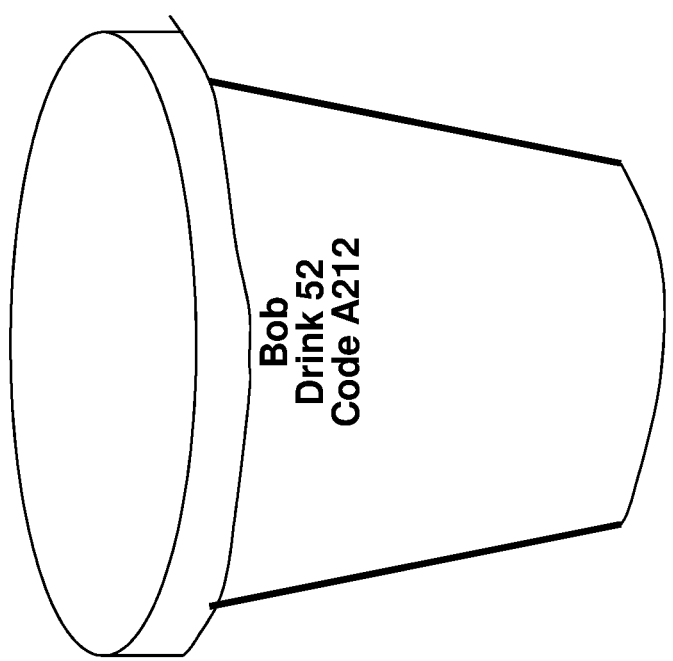

In FIG. 12A, the cashier specified that a drink is 'Drink Code 52' (i.e. in a certain coffee shop, barista might understand '52' to relate to Frappuccino. In FIG. 12B, the printer has a camera 520 which can take a picture of the outside of the cup—this data can be decoded using Optical Character Recognition (OCR) technology to 'read.'

From FIGS. 9A-9B, the printer (or circuitry in communication therewith) 'knows' that the user specified a drink order to print image having code A212 on a Frappuccino. The data from FIGS. 9A-9B can be matched to the OCR data—if they match this is a sign that the barista has placed the 'correct drink' on the printer—thus, the user-specified drink order (e.g. specified in part or entirely by terminal 100) specifies that a specific image is printed on a drink having a specific content (see step S301-S305 of FIG. 13A). In step S209, when the barista presses code 'A212' the device can (i) make sure that drink having code 'A212' written on the side is in fact 'loaded' onto the printer (e.g. using the OCR technology) and/or (ii) make sure that the drink whose content is specified by code '52' is loaded on the printer.

In different embodiments, the OCR may read any text written on the side of the cup and may assess and/or may determine from the text on the side of the cup 'current drink property(ies).' In the example of FIG. 12A, this may from the word Bob (i.e. who usually orders cappuccino) and/or from the 'Drink 52' (i.e. which is usually associated with a cappuccino) and/or from "Code A212' (i.e. which is associated within the mapping and/or database with 'cappuccino').

In FIG. 13A, printing on the content of the drink is only 'permitted' if the drink actually detected to be 'on the printer' matches the content specified in the order (e.g. see FIGS. 9A-9B).

Thus, in step of S217 the printing is in a manner that is 'contingent upon' the drink-match parameter this means that only if the drink-match parameter meets certain criteria (e.g. indicative of a 'good match'—e.g. a score above a certain threshold) does the device controller permit printing and/or does the device controller responds to the user-selection of a drink code by instructing the ink-jet printer to print the image.

Alternatively or additionally (see FIG. 13B), if there is a 'mismatch' an alert or alarm signal (e.g. visual and/or audio) may be generated to 'warn' the barista not to print on a particular drink.

The example of FIGS. 12A-12B relate to the specific example where information on the container 490 (e.g. text written thereon) is used to identify the 'content' of the drink (i.e. the 'candidate beverage' the barista has placed on the tray 470 and therefore might print thereon by pressing the 'candidate code' from the menu on screen 260).

Alternatively or additionally, information about the contents of the drink may be obtained not from the container and/or writing thereon but from one or more (i.e. any combination) of the following technique: a temperature sensor may measure the temperature (e.g. IR sensor) of the drink—e.g beer is cold but coffee is hot—if the 'drink order data' (see FIGS. 9A-9B) indicate that the drink associated with code "ABCD" is beer, when the barista selects the code "ABCD" the temperature of the 'candidate drink' on the tray is measured—if the temperature is 'hot' then the drink is clearly not beer and an alert and/or alarm signal is generated or the printer just will not allow printing.

In another example another camera (now shown) may be stationed next to cartridge 430 looking 'down'—since the color of coffee is different from that of 'beer' if the user attempts to choose the code for a drink (i.e. according to the drink order) that is supposed to be coffee but the 'down-looking camera' shows to be beer, then the alert will be provided.

Some embodiments relate to a printing device for printing on a current drink comprising: a. a platform (e.g. tray—elevatable tray having a variable elevation that is controlled by a motor) upon which the current drink rests; b. an ink-jet printer (e.g. thermal inkjet and/or bubble-jet) to downwardly ink-jet droplets of ink towards the tray to print an image on the drink supported by the tray; c. a display-screen; (e.g. disposed above the tray and/or above a nozzle of the ink-jet printer) d. one or more sensor(s) for acquiring current-drink property-data describing the current drink currently supported by the platform (e.g. tray) and/or beneath a print-head of the ink-jet printer e. a mapped drink-code database specifying a map for a plurality of drink-printing codes, between: i. each displayed drink-printing code of the plurality of drink-printing codes; and ii. a respective combination of (i) a respective drink-printing-code-specific target-image to be printed by the ink-jet printer; and (ii) respective drink-printing-code-specific target-drink property-data describing contents of a respective target-drink and/or its container; f. analysis circuitry for computing a drink-match parameter between: i. property-data of the current drink sensed by the sensor(s) and ii. property-data of one or more of the target drinks specified by the database; g. a user-interface for: i. displaying a drink-property-heterogeneous menu comprising the plurality of drink-printing codes on the display-screen; an ii. receiving a user-selection of one of the drink codes to thereby user-specify, according to the mapped drink-code database, a target-image and target-drink property-data; h. a device controller for responding to the user drink-code selection, in accordance with content of the mapped drink-code database, output of the sensor(s) and output of the analysis circuitry, by printing the user-interface-specified target-image onto an upper surface of the current drink in a manner that is contingent upon the drink-match parameter that is specific to the combination of: i. the user-specified target-drink property-data as specified via the user-interface; ii. the current drink property-data as sensed by the sensor(s).

In some embodiments, the sensor is an image sensor configured to acquire a digital image of an outer wall of a container of the current drink resting on the platform (e.g. tray).

In some embodiments, the analysis circuitry is configured to subject the acquired digital image to optical-character-recognition (OCR) analysis derive therefrom the target-drink property-data.

In some embodiments, instead of writing the drink code (e.g. '52' is Frappuccino) on the side of the cup, a drink-ordering computer (e.g. cash-register in the coffee shop) might print this code to a printer (e.g. on paper)—e.g. near machine 310. In this case, it might be possible to augment the printed code as follows—the user can show the 'image code' to the cashier would could print it from the 'order-generating cmoputer' together with the 'drink code'—thus, it would state 'Drink 52 Image XYZ"—this would be printed on paper. The barista would take the small portion of paper containing 'Drink 52 Image XYZ" and s/he would know (i) first generate drink 310 using machine 310 and (ii) then select the option 'XYZ' from the menu to print the image associated with text code 'XYZ.'

Additional Discussion

Standard Reference Method or SRM[1] is one of several systems modern brewers use to specify beer color. Determination of the SRM value involves measuring the attenuation of light of a particular wavelength (430 nm) in passing through 1 cm of the beer, expressing the attenuation as an absorption and scaling the absorption by a constant (12.7 for SRM; 25 for EBC). The SRM (or EBC) number represents a single point in the absorption spectrum of beer. As such it cannot convey full color information which would require 81 points, but it does remarkably well in this regard (it conveys 92% of spectral information) even when fruit beers are considered. Auxiliary "deviation coefficients" (see Augmented SRM below) can pick up the remainder and are necessary for fruit beers and when subtle color differences in malt beers are to be characterized.

Various features of drink-printer device 400, according to non-limiting examples, are discussed below.

In some embodiments, drink-printer may be employed in a retail environment (e.g. a coffee-house, restaurant, café, etc) or another environment where multiple drinks are printed upon within a relatively 'short' period of time.

Figure 15:
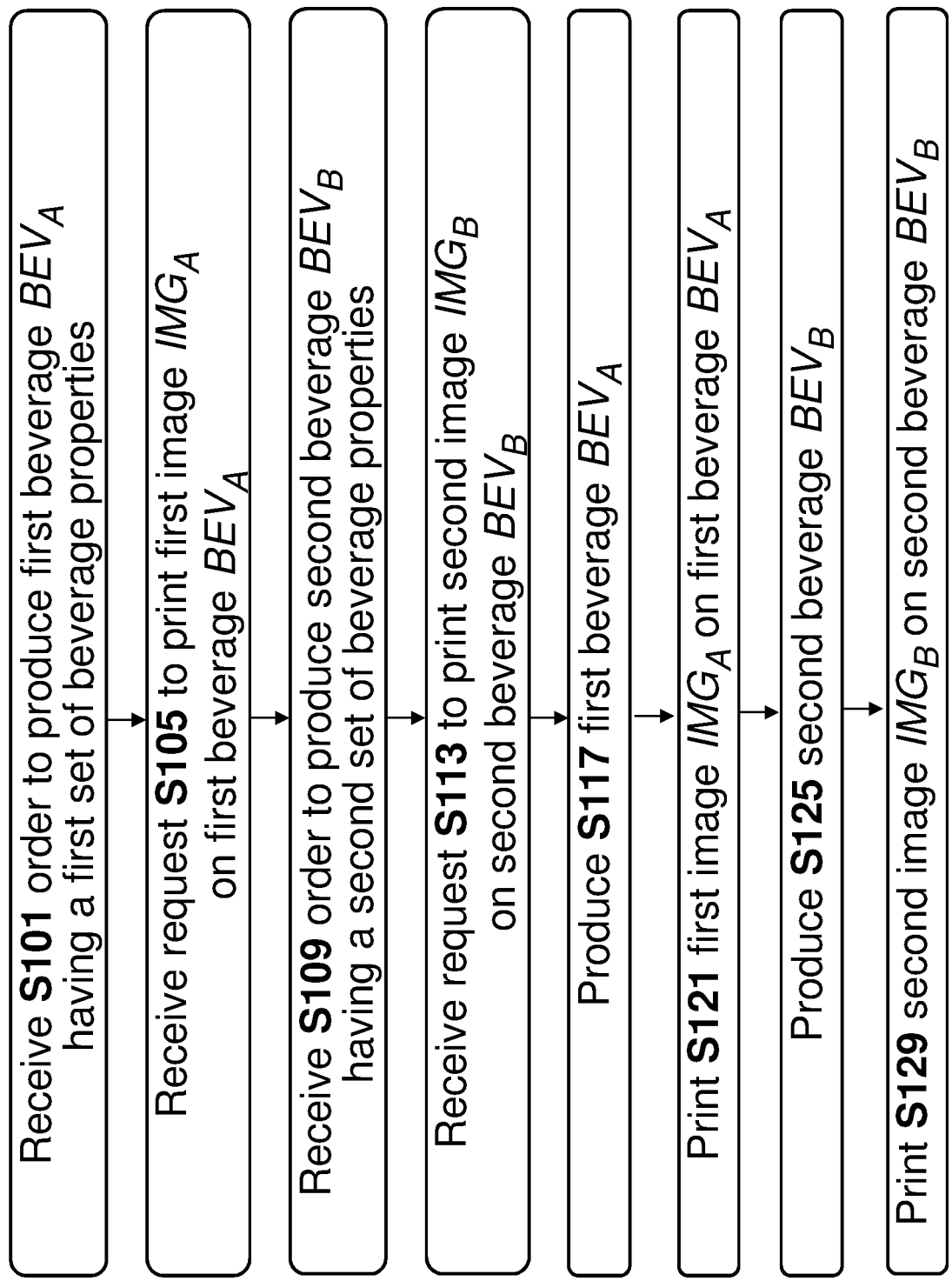

FIG. 15 is a flow-chart of a method for employing the drink-printing device. In step S101, an order to produce a first beverage $BEV_A$ (e.g. a cappuccino from Columbian coffee beans) is received—e.g. an 'app' operating on a mobile phone may be employed to place an order which is received via the Internet. In step S105, a request is received to print a first image $IMG_A$ (e.g. a photograph such as a 'selfie') on the upper surface of the first beverage $BEV_A$. The skilled artisan will appreciate that the request to produce the beverage and the request print on an upper surface thereof may be received as separate requests or as part of a single request—e.g. a single mobile phone app may include a user-interface for both specifying a drink as well as an image to be printed thereof.

In step S109, an order to produce a second beverage $BEV_B$ (e.g. Belgian beer) is received—e.g. an 'app' operating on a mobile phone may be employed to place an order which is received via the Internet. In step S113, a request is received to print a second image $IMG_B$ (e.g. a sports logo) on the upper surface of the second beverage $BEV_B$.

The first $BEV_A$ and second $BEV_B$ beverages are respectively produced in steps S117 and S125. In this example, the 'production' of the first beverage may entail brewing coffee and/or topping coffee with foamed milk or milk-substitute. In this example, the 'production' of the second beverage may entail pouring beer into a vessel (e.g. a mug)—e.g. using a 'beer-tap' device. In step S121 the first image $IMG_A$. is printed after the first beverage $BEV_A$ is produced. In step S129 the second image $IMG_B$. is printed after the second beverage $BEV_B$ is produced.

In some embodiments, there is a risk that the wrong image will be printed on the wrong beverage—e.g. $IMG_B$ may be printed on $BEV_B$. This risk may be more serious in situations where a single drink-printing device is used for print designs on multiple types of drinks.

Figure 16:
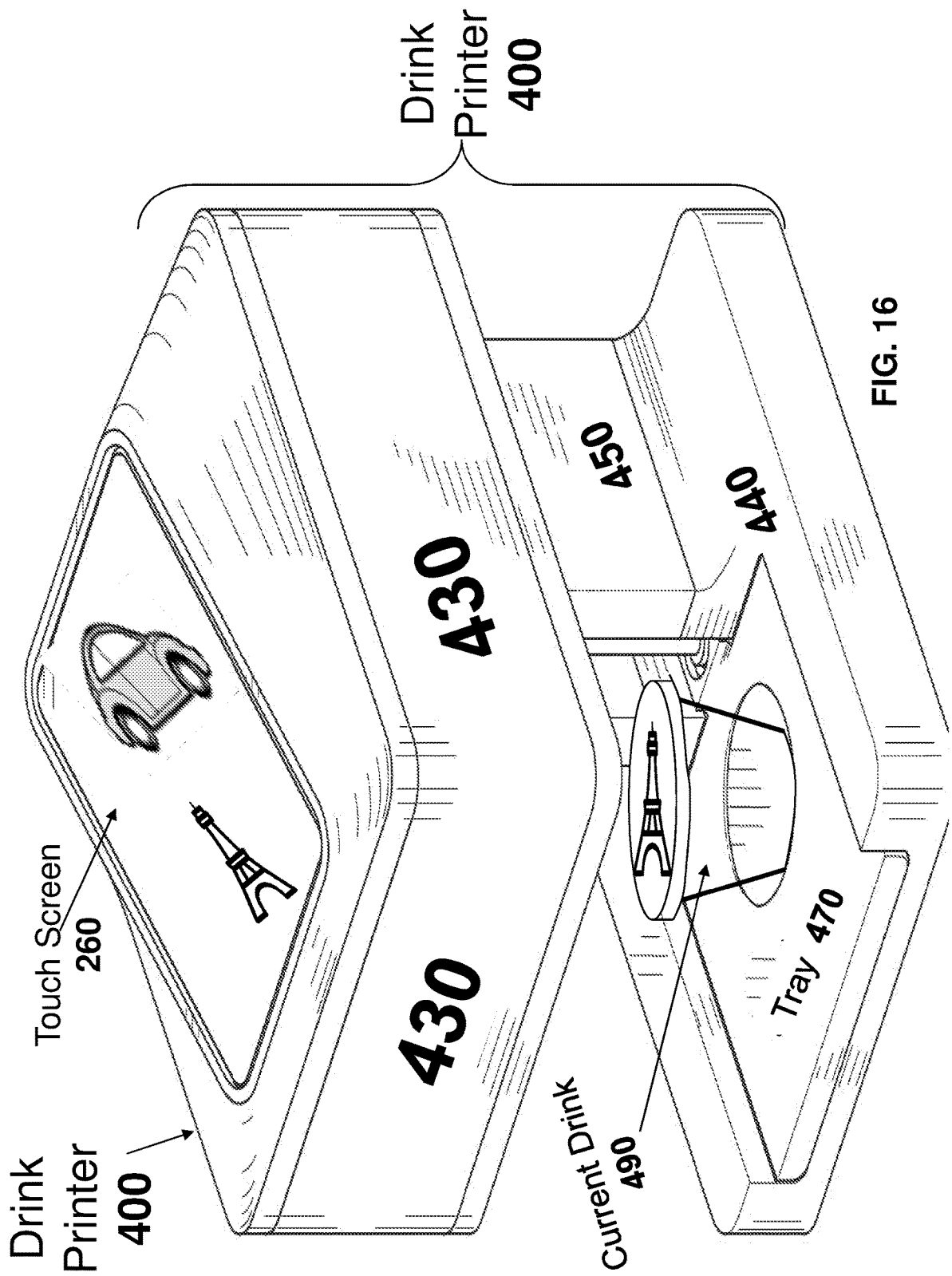

In one example and as shown in FIG. 16, a user interface (e.g. implemented using touch screen 260) is used by an operator of the drink printing device (e.g. a barista). The images to be printing are displayed on the touch screen 260. Upon user engagement with an image (e.g. pressing on the Eiffel tower image), drink printer prints the image upon the upper surface thereof. However, in certain environments (e.g. retail environment) there is a risk that the user (e.g. barista) will print the wrong image on the wrong beverage.

Figure 17B:
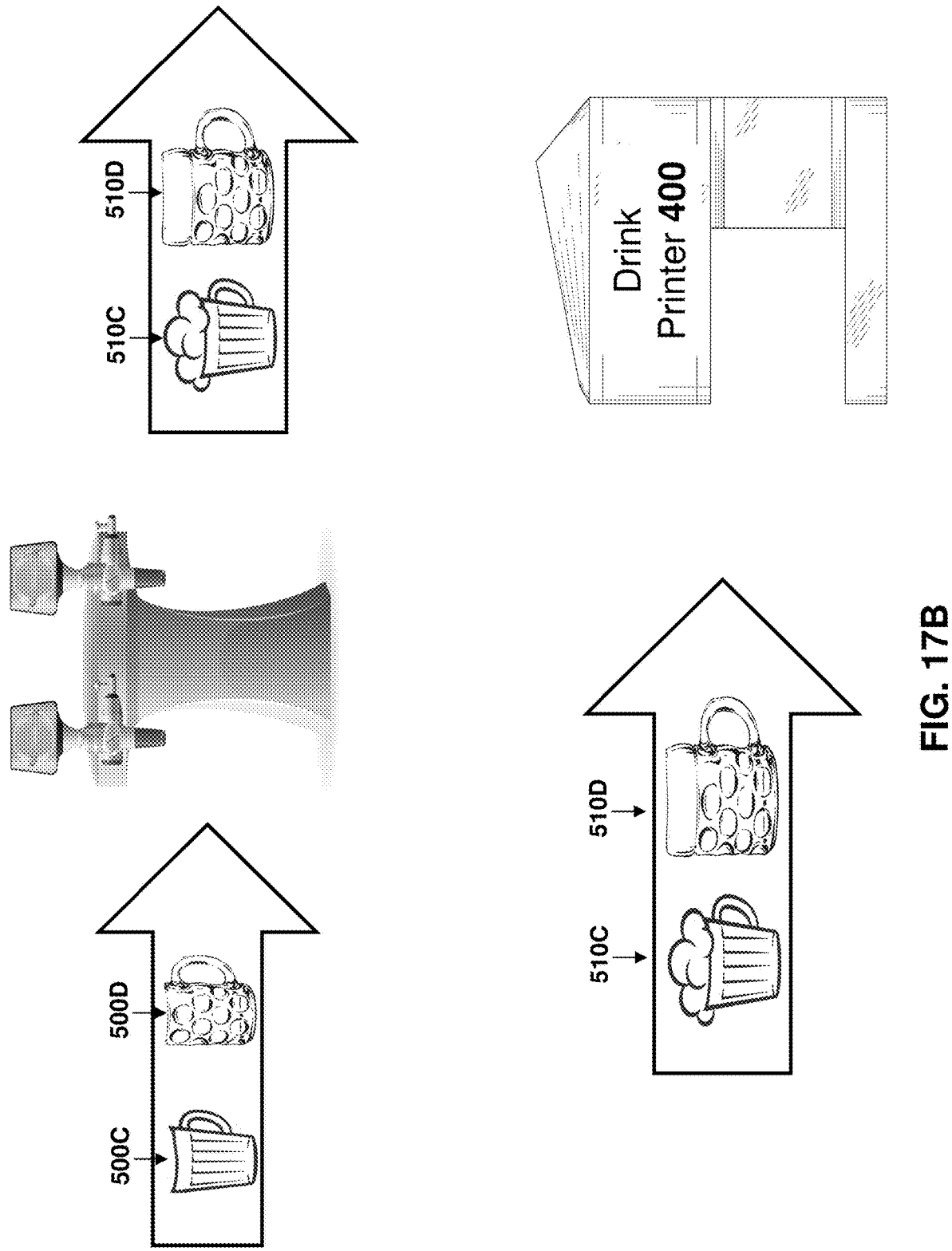

In one example, shown in FIG. 17A, a drink production machine provides beverages 510A, 510B respectively into containers (e.g. cups 500A, 500B). The produced beverages are subsequently printed upon. FIG. 17B relates to beer—the drink production machine includes a tap assembly where each tap dispenses a different respective type/brew/brand of beer. In FIG. 17B, the drink production machine provides beverages 510C, 510D respectively into containers (e.g. mugs 500C, 500D), In the example of FIG. 17C, a single drink printer 400 prints on both coffee and beer. For example, the single drink printer includes multiple ink reservoirs—e.g. a coffee-based ink (e.g. where the primary colorant is coffee) for printing on coffee, and a malt-based ink for printing on beer. In the example of FIG. 17C, not only does printing the wrong design on the wrong drink risk providing the wrong image, but it may also ruin the taste of the drink.

Thus, in some embodiments the ink or colorant is selected from multiple reservoirs to 'taste-match' the current drinks—e.g. a coffee ink for printing on coffee, a malt-based ink for printing on beer. In another example, the taste of the colorant which most closely matches a 'type' of beer is selected—this may require distinguishing between different types of beer.

Figure 18A:
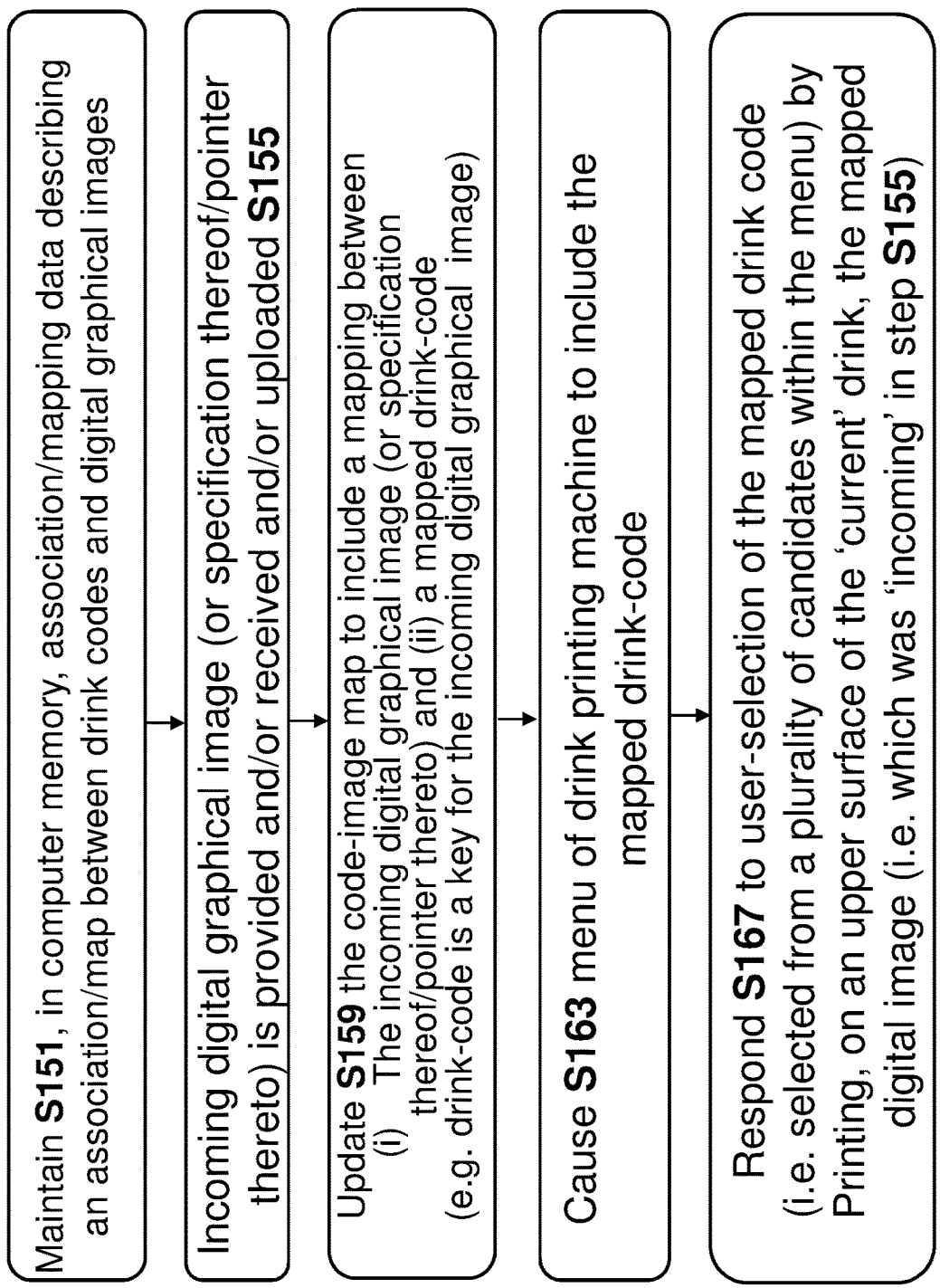
Figure 18C:
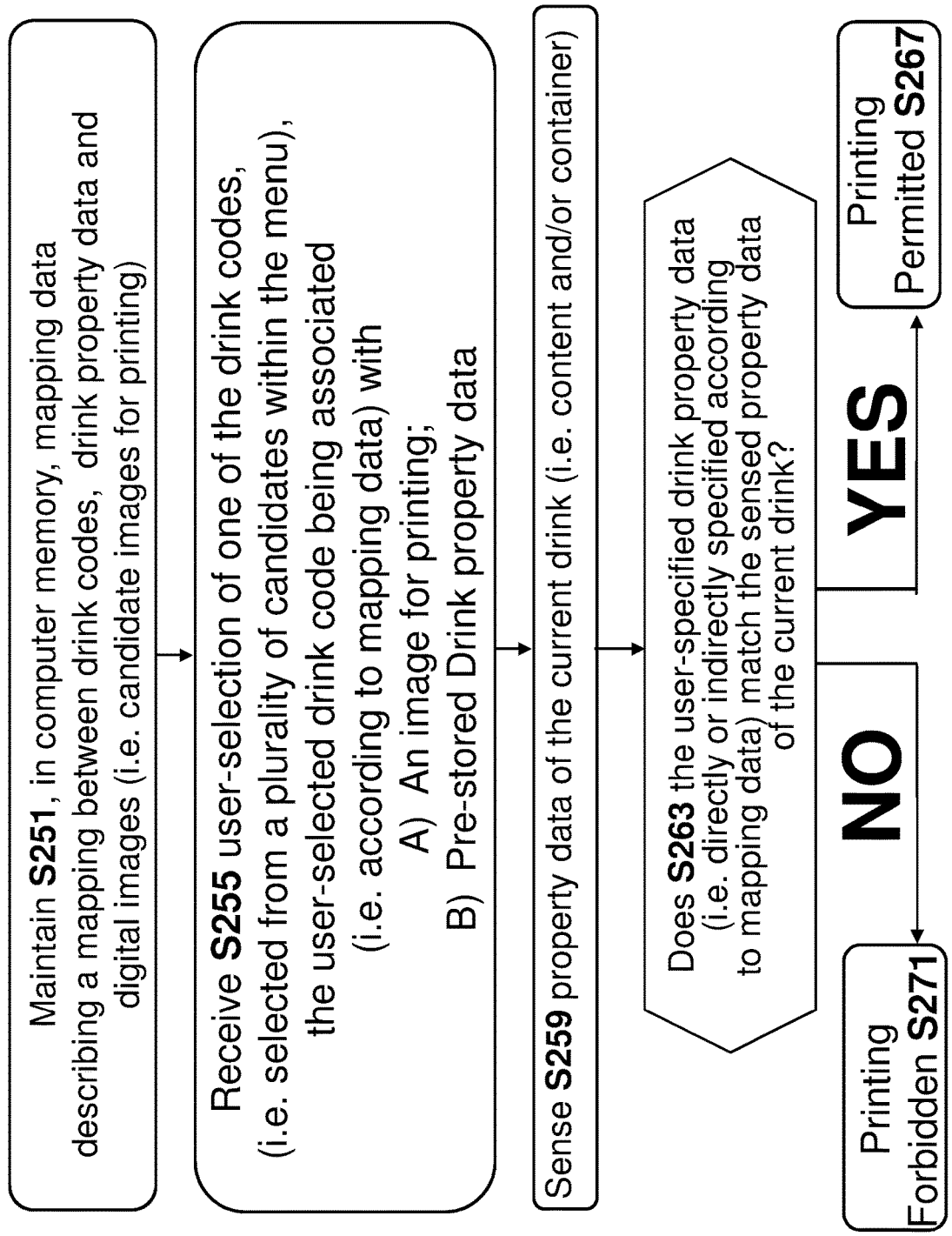
Figure 19A:
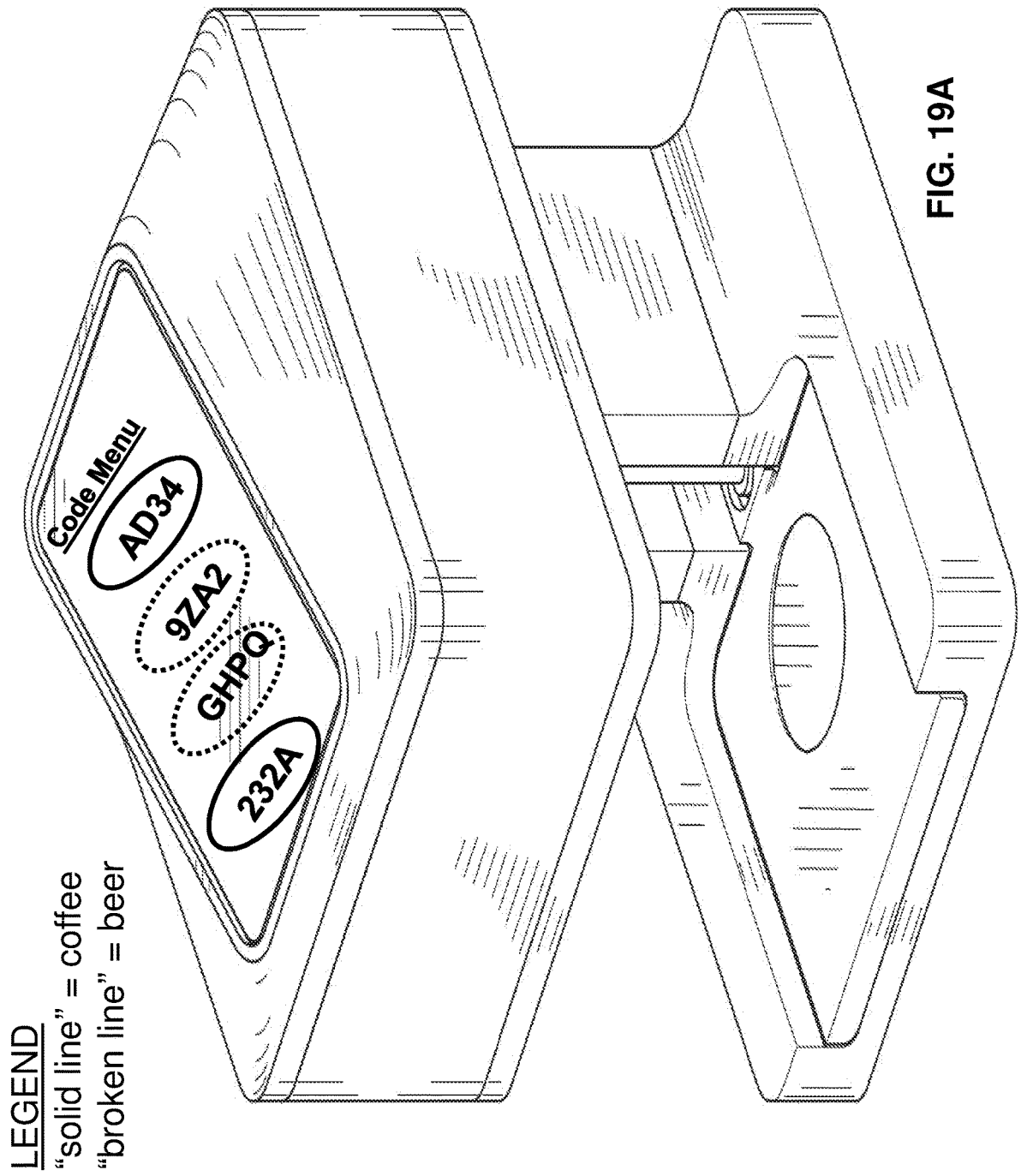
Figure 19B:
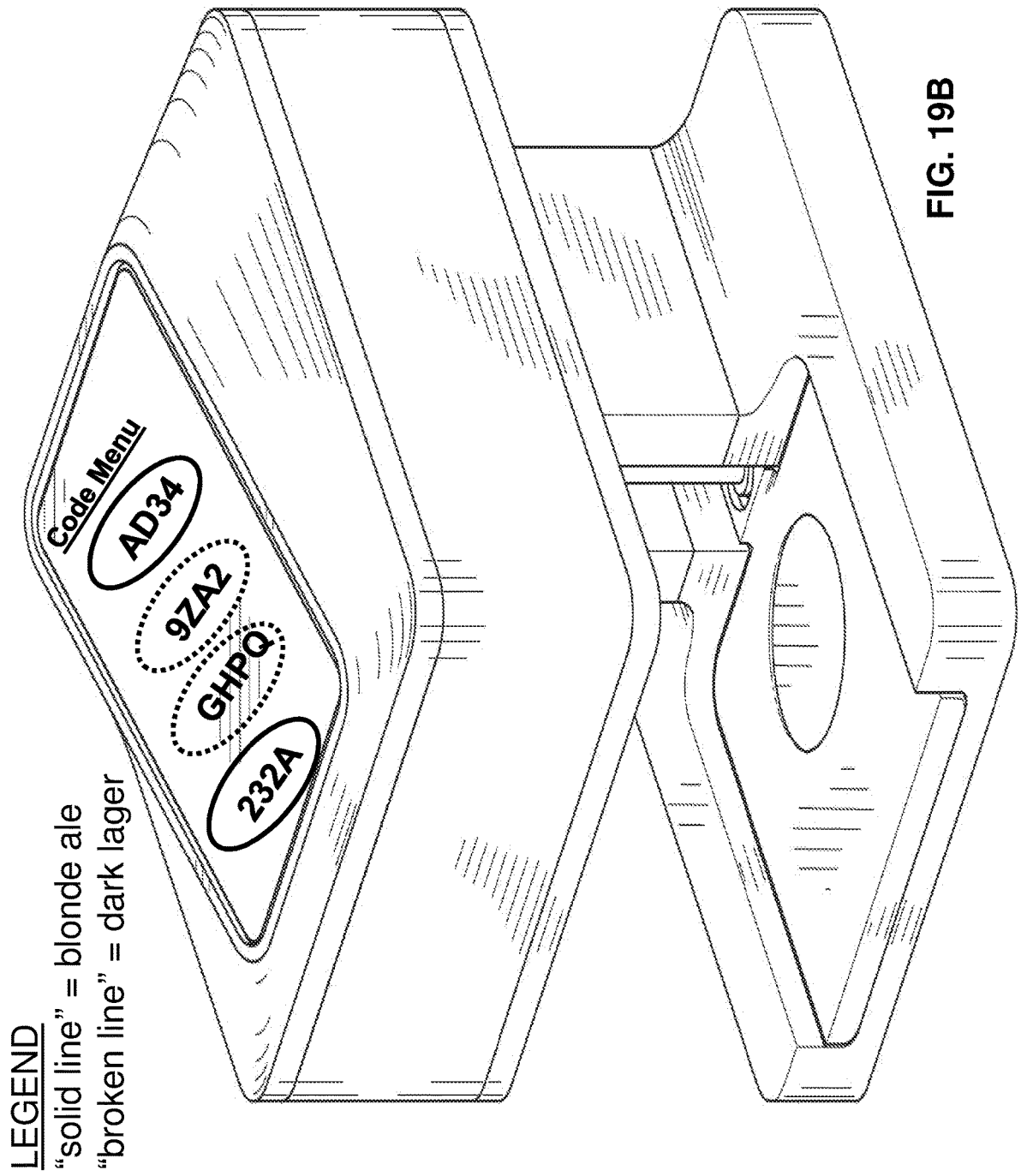
Figure 19C:
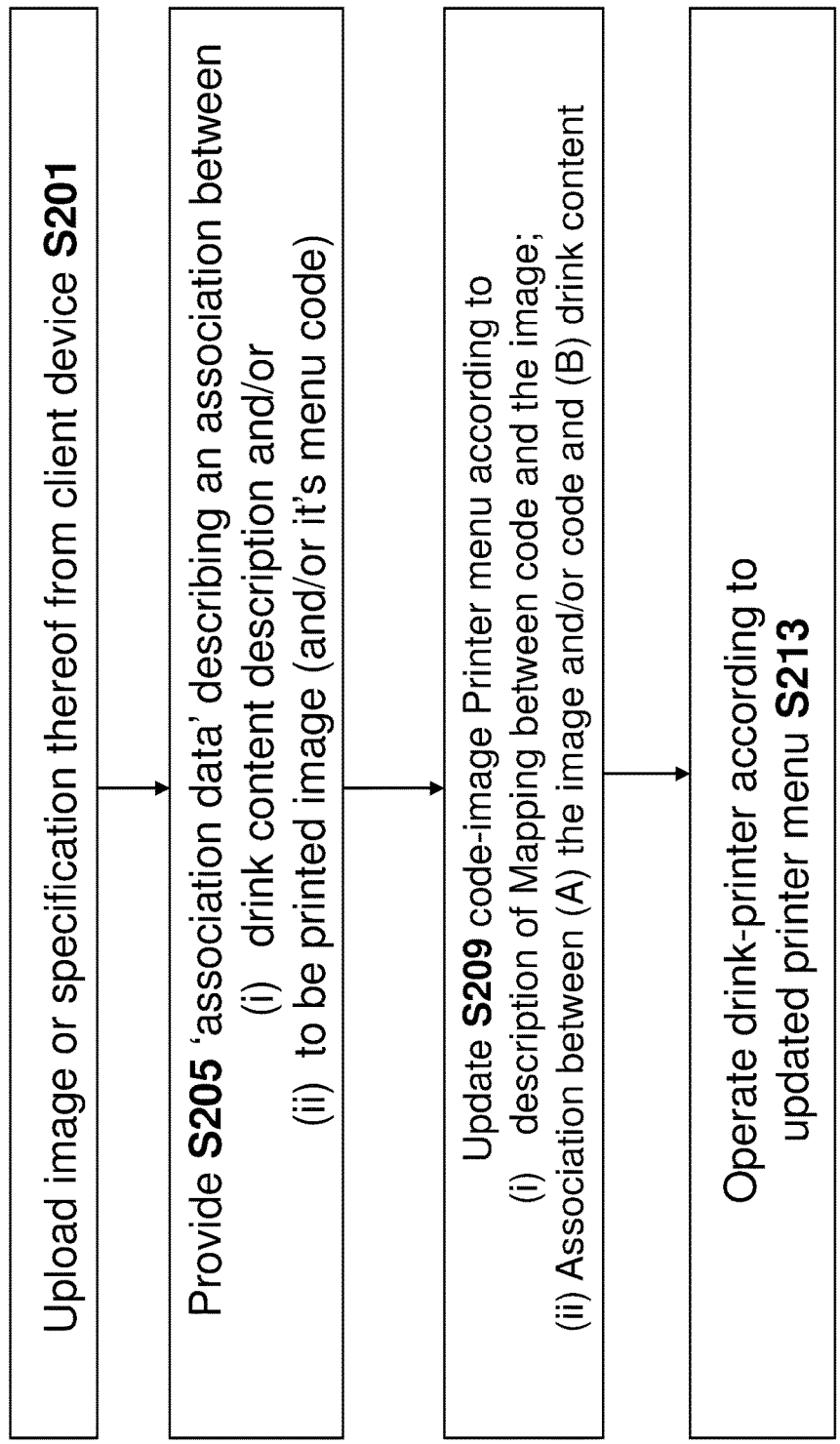
Figure 20B:
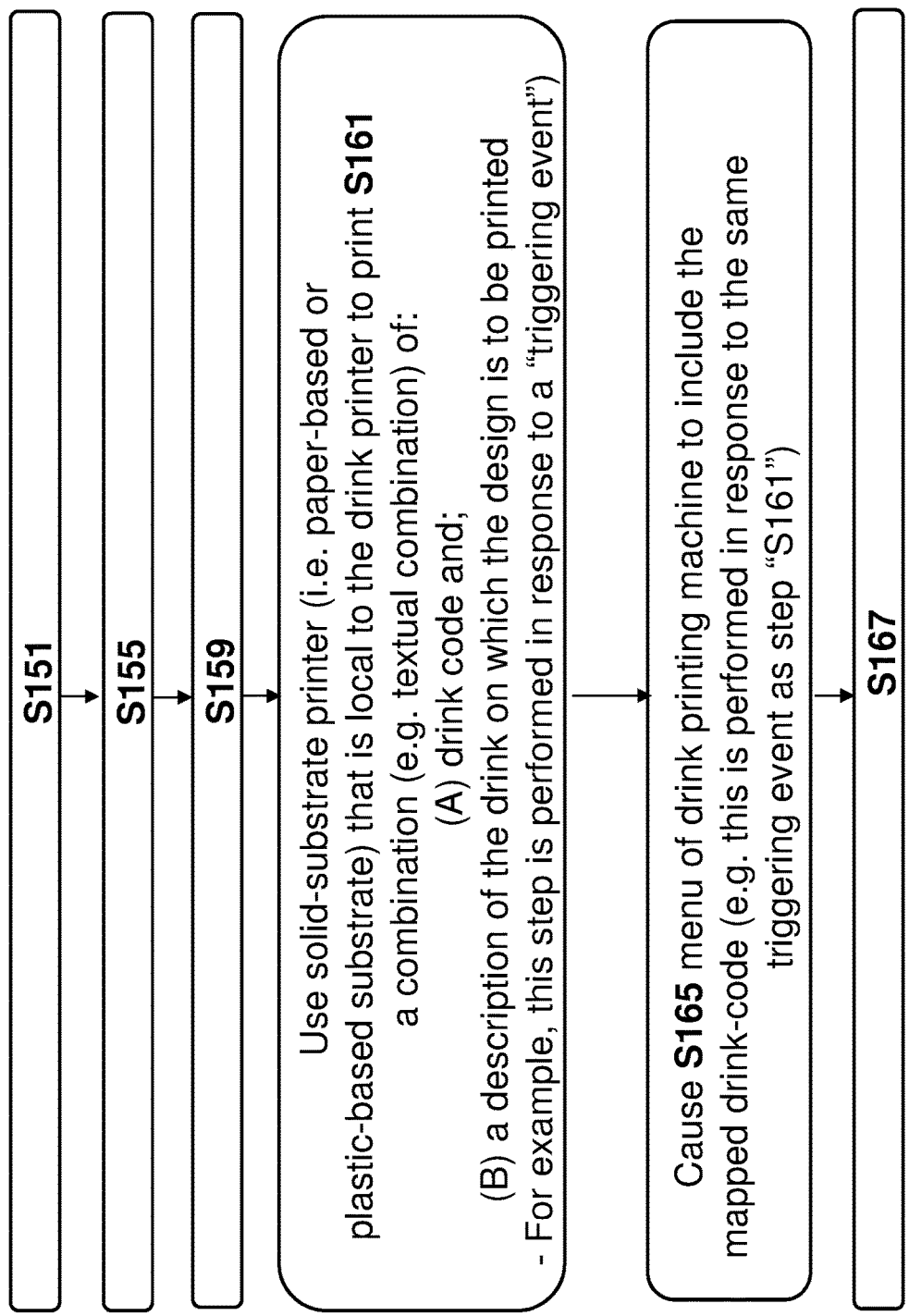

A Discussion of FIGS. 18A-18C

In the example of FIG. 18C, a plurality of codes (e.g. textual codes) are displayed (e.g. simultaneously displayed) on a screen where each code is associated with a different image to print onto the beverage. Thus, in one example (see FIG. 1A), when the user engages code AD34 a first image (e.g. first .gif) is printed—e.g. a picture of an animal, when the user engages a second code 9ZA2 a second image (e.g. a second .gif is printed (e.g. the script/cursive words "Printed Design") is printed, and so on.

FIGS. 18A-18C, 19A-19C, 20A-20B illustrate additional examples.

What is claimed is:

1. A drink-printing system for printing on a current drink comprising:
    a. an ink-jet printer defining a target-location;
    b. a plurality of colorant reservoirs;
    c. one or more sensor(s) configured to sense property-data of a current drink that is currently at the target location so as to perform at least one of the following drink-distinguishing operations for the current drink:
       distinguishing between multiple types of beverages;
       distinguishing between multiple types of coffee; and
       distinguishing between multiple types of beer;
    d. control circuitry configured to:
       i. cause the ink-jet printer to print, on an upper surface of the current drink, a pre-stored digital image; and
       ii. respond to output of the sensor(s), causing the inkjet printer to dynamically select a colorant reservoir from the plurality of colorant reservoirs, for the ink-jet printing, in accordance with the results of drink-distinguishing operation(s).

2. The drink-printing system of claim 1 wherein in response to a determining by the sensor(s) that the current drink is a coffee, the control circuitry selects a coffee-based colorant reservoir.

3. The drink-printing system of claim 1 comprising a plurality of malt-based colorant reservoirs and the control circuitry selects between them for the ink-jet printing according to the results of the distinguishing between the multiple types of beer.

4. The system of claim 1 wherein the sensor(s) distinguishes between different types of beverages by measuring foam quality and/or property(ies).

5. The drink-printing system of claim 1 wherein the sensor(s) are configured to distinguish between coffee and beer.

6. The drink-printing system of claim 1, wherein the performing of at least one of the drink-distinguishing operations includes photographing the contents of the current drink and analyzing a portion of the photograph corresponding to the contents of the drink so as to sense a property of a foam that is disposed at an upper surface of the drink.

7. The drink-printing system of claim 1, wherein the performing of at least one of the drink-distinguishing operations includes photographing the contents of the current drink and analyzing a portion of the photograph corresponding to the contents of the drink so as to sense a color property of contents of the current drink.

8. The drink-printing system of claim 1, wherein the performing of at least one of the drink-distinguishing operations includes photographing the contents of the current drink and analyzing a portion of the photograph corresponding to the contents of the drink.

9. The drink-printing system of claim 8, wherein the photographing is from above a rim of a beverage-container of the current drink.

10. The drink-printing system of claim 8, wherein the photographing is from camera disposed above the current drink and downwardly-aimed to the current drink.

11. The drink-printing system of claim 1, wherein the sensor(s) distinguishes between different types of beverages in accordance with light reflected by the contents of the current drink and received by the sensor(s).

12. A drink-printing system for printing on a current drink comprising:
    a. an ink-jet printer defining a target-location;
    b. a plurality of colorant reservoirs;
    c. one or more sensor(s) configured to sense contents of a current drink that is currently at the target location so as to perform at least one of the following drink-distinguishing operations for the current drink:
       distinguishing between multiple types of beverages;
       distinguishing between multiple types of coffee; and
       distinguishing between multiple types of beer;
    d. control circuitry configured to:
       i. cause the ink-jet printer to print, on an upper surface of the current drink, a pre-stored digital image; and
       ii. respond to output of the sensor(s), causing the inkjet printer to dynamically select a colorant reservoir from the plurality of colorant reservoirs, for the ink-jet printing, in accordance with the results of drink-distinguishing operation(s).

13. The drink-printing system of claim 12, wherein the sensor(s) distinguishes between different types of beverages by sensing a property of a foam that is disposed at an upper surface of the drink.

14. The drink-printing system of claim 12, wherein the sensor(s) distinguishes between different types of beverages by sensing thermal energy and/or temperature of contents of the current drink.

15. The drink-printing system of claim 12, wherein the sensor(s) distinguishes between different types of beverages in accordance with light reflected by the contents of the current drink and received by the sensor(s).

16. The drink printing system of claim 12, wherein the at least one of the drink-distinguishing operations for the current drink includes distinguishing between coffee and beer.

17. The drink printing system of claim 12, wherein the at least one of the drink-distinguishing operations for the current drink includes distinguishing between coffee and a beverage that is not coffee.

18. The drink printing system of claim 12, wherein the at least one of the drink-distinguishing operations for the current drink includes distinguishing between coffee and an alcoholic beverage that is not beer.

19. The drink printing system of claim 12, wherein the at least one of the drink-distinguishing operations for the current drink includes distinguishing between beer and a beverage that is not beer.

20. The drink printing system of claim 12, wherein the at least one of the drink-distinguishing operations for the current drink includes distinguishing between beer and an alcoholic beverage that is not beer.

\* \* \* \* \*